(12) United States Patent
Fukuda et al.

(10) Patent No.: US 11,749,400 B2
(45) Date of Patent: Sep. 5, 2023

(54) MEDICAL CARE SUPPORT DEVICE, MEDICAL CARE SUPPORT METHOD, AND MEDICAL CARE SUPPORT PROGRAM

(71) Applicant: FUJIFILM CORPORATION, Tokyo (JP)

(72) Inventors: Takeshi Fukuda, Kanagawa (JP); Haruyasu Nakatsugawa, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 478 days.

(21) Appl. No.: 17/060,092

(22) Filed: Oct. 1, 2020

(65) Prior Publication Data

US 2021/0103769 A1 Apr. 8, 2021

(30) Foreign Application Priority Data

Oct. 3, 2019 (JP) .................................. 2019-182723

(51) Int. Cl.
| | |
|---|---|
| *G16H 30/20* | (2018.01) |
| *G16H 30/40* | (2018.01) |
| *G16H 50/20* | (2018.01) |
| *G16H 20/10* | (2018.01) |
| *A61B 6/12* | (2006.01) |

(Continued)

(52) U.S. Cl.
CPC .............. *G16H 30/40* (2018.01); *A61B 6/12* (2013.01); *G06F 18/217* (2023.01); *G06F 18/2115* (2023.01); *G06F 18/2155* (2023.01); *G16H 20/10* (2018.01); *G16H 20/40* (2018.01); *G16H 30/20* (2018.01); *G16H 50/20* (2018.01);

(Continued)

(58) Field of Classification Search
CPC ........ G16H 30/20; G16H 30/40; G16H 50/20; G16H 20/40; G16H 20/10; A61B 6/12; A61B 5/055; G06F 18/217; G06F 18/2155; G06F 18/2115; G06K 9/62; G06K 9/6231; G06K 9/6259; G06K 9/6262; G06K 2209/05
See application file for complete search history.

(56) References Cited

U.S. PATENT DOCUMENTS 8,830,308 B2 * 9/2014 Taniguchi ........ A61B 1/000094
348/65

FOREIGN PATENT DOCUMENTS

| JP | 2017-202310 A | 11/2017 | |
|---|---|---|---|
| JP | 2017202310 | * 11/2017 | ............... A61B 6/03 |

* cited by examiner

*Primary Examiner* — Tuan H Nguyen
(74) *Attorney, Agent, or Firm* — SOLARIS Intellectual Property Group, PLLC

(57) ABSTRACT

A medical care support device includes: an acquisition unit that acquires medical information including medical image data obtained by capturing a digestive tract of a subject; a derivation unit that derives presence or absence of a foreign object in the digestive tract, based on the medical information and a learned model learned in advance using plural pieces of learning medical information including the medical image data in which a label according to a kind of the foreign object is assigned to the foreign object in the digestive tract according to each organ of the digestive tract, and derives at least one of position, size, or kind of the foreign object if the foreign object is present; and an output unit that outputs removal information of the foreign object according to the at least one of position, size, or kind of the foreign object, based on a result of the derivation.

9 Claims, 28 Drawing Sheets

(51) Int. Cl.
  G16H 20/40 (2018.01)
  G06F 18/2115 (2023.01)
  G06F 18/21 (2023.01)
  G06F 18/214 (2023.01)
  *A61B 6/00* (2006.01)
  *A61B 5/055* (2006.01)
(52) U.S. Cl.
  CPC .............. *A61B 5/055* (2013.01); *A61B 6/508* (2013.01); *G06V 2201/03* (2022.01)

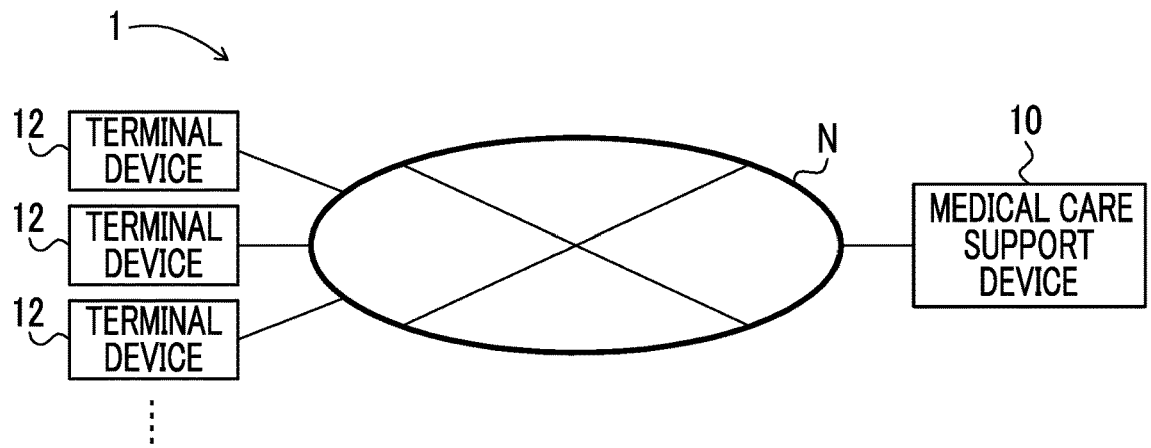
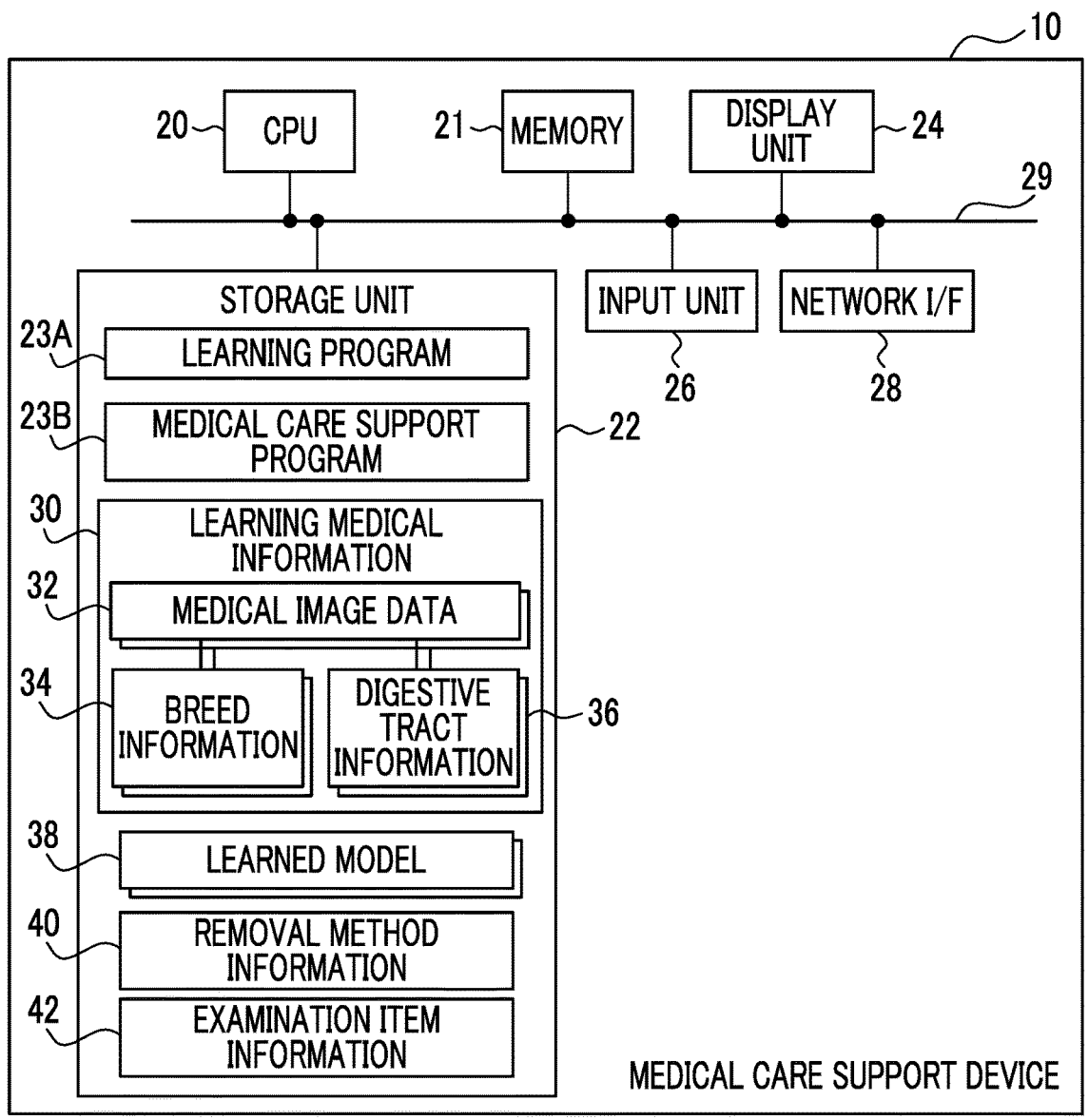

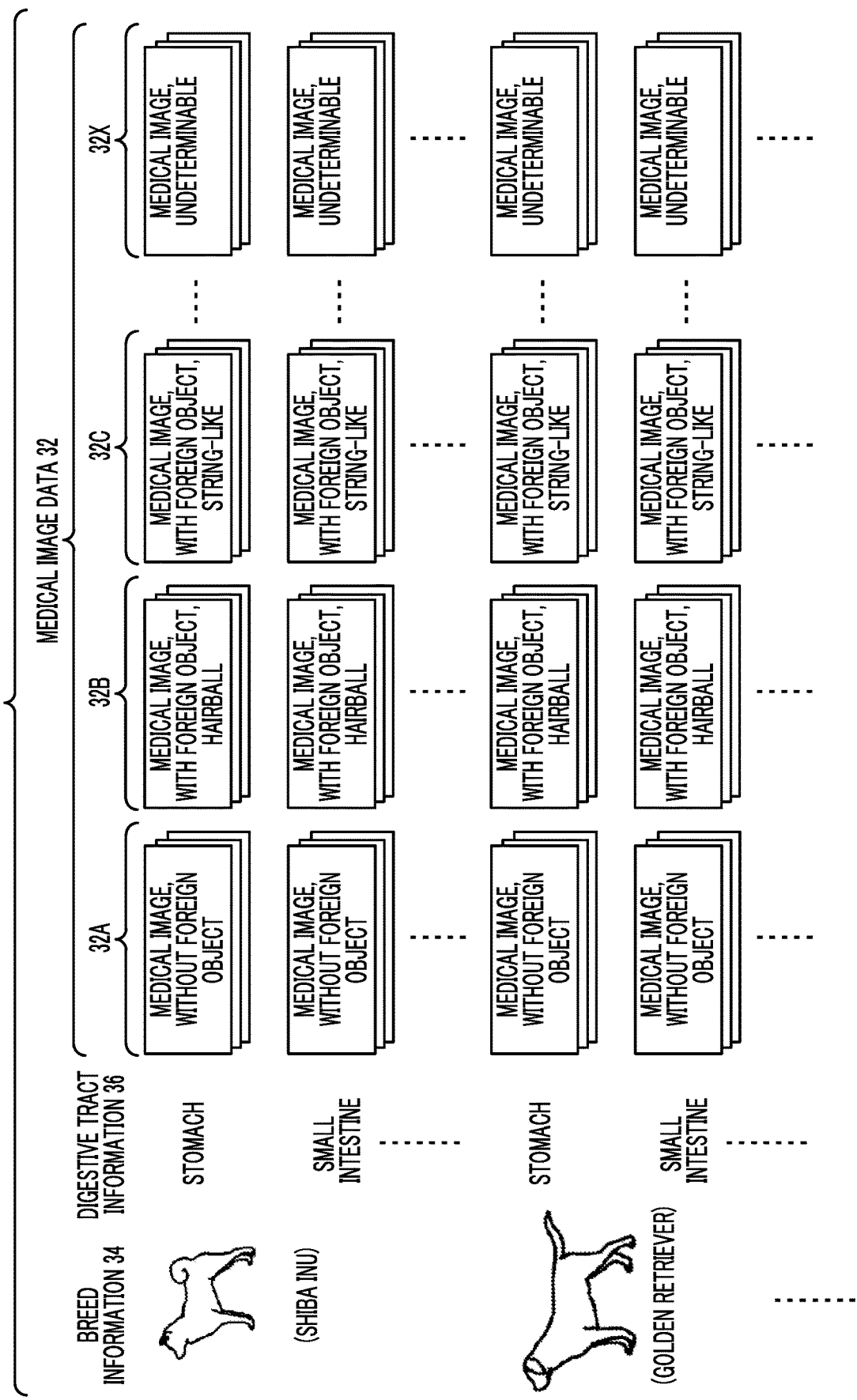

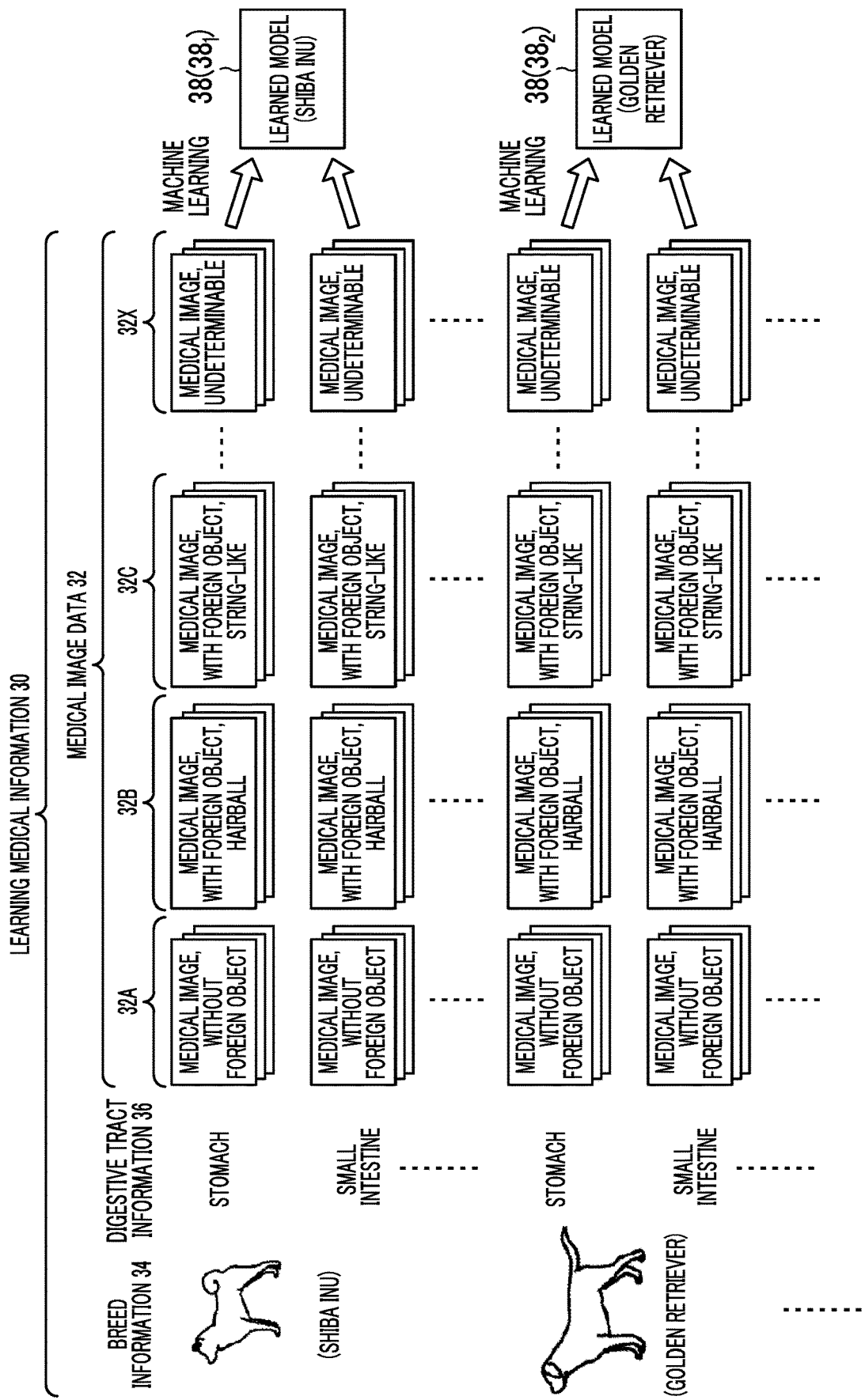

FIG. 6

| POSITION | SIZE | KIND | REMOVAL METHOD |
|---|---|---|---|
| STOMACH | LESS THAN 2 cm | SKEWER-LIKE | EMETIC AGENT |
| STOMACH | 2 cm OR MORE | SKEWER-LIKE | ENDOSCOPE |
| STOMACH | LESS THAN 2 cm | CIRCULAR | FOLLOW-UP OBSERVATION |
| SMALL INTESTINE | --- | STRING-LIKE | OPERATION |
| ...... | ...... | ...... | ...... |

| POSITION | SIZE | KIND | REMOVAL METHOD |
|---|---|---|---|
| STOMACH | LESS THAN 1 cm | SKEWER-LIKE | EMETIC AGENT |
| STOMACH | 1 cm OR MORE | SKEWER-LIKE | ENDOSCOPE |
| STOMACH | LESS THAN 1 cm | CIRCULAR | FOLLOW-UP OBSERVATION |
| SMALL INTESTINE | --- | STRING-LIKE | OPERATION |

| POSITION | SIZE | KIND | REMOVAL METHOD 40(40₂) |
|---|---|---|---|
| STOMACH | LESS THAN 3 cm | SKEWER-LIKE | EMETIC AGENT |
| STOMACH | 3 cm OR MORE | SKEWER-LIKE | ENDOSCOPE |
| STOMACH | LESS THAN 3 cm | CIRCULAR | FOLLOW-UP OBSERVATION |
| SMALL INTESTINE | --- | STRING-LIKE | OPERATION |
| ...... | ...... | ...... | ...... |

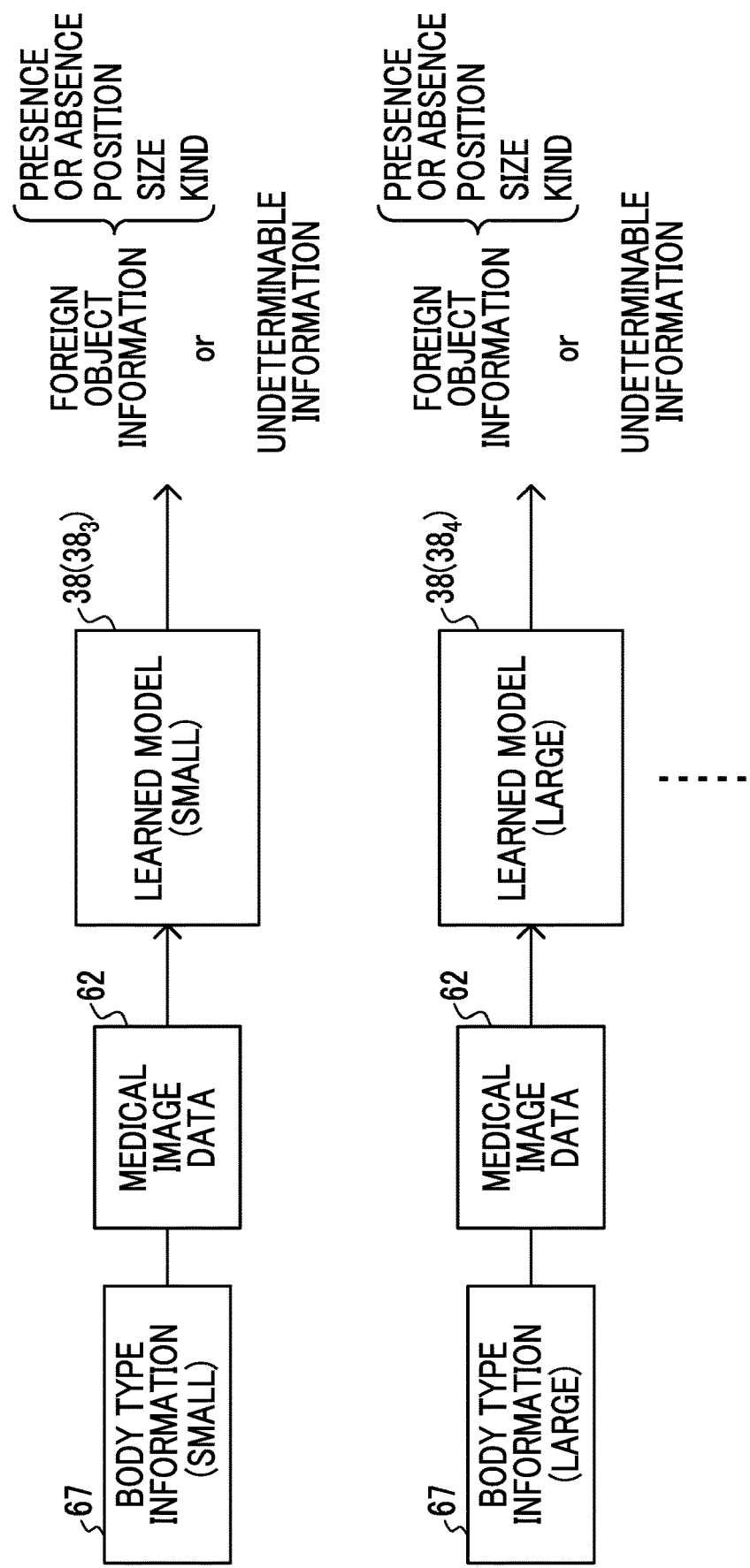

FIG. 21

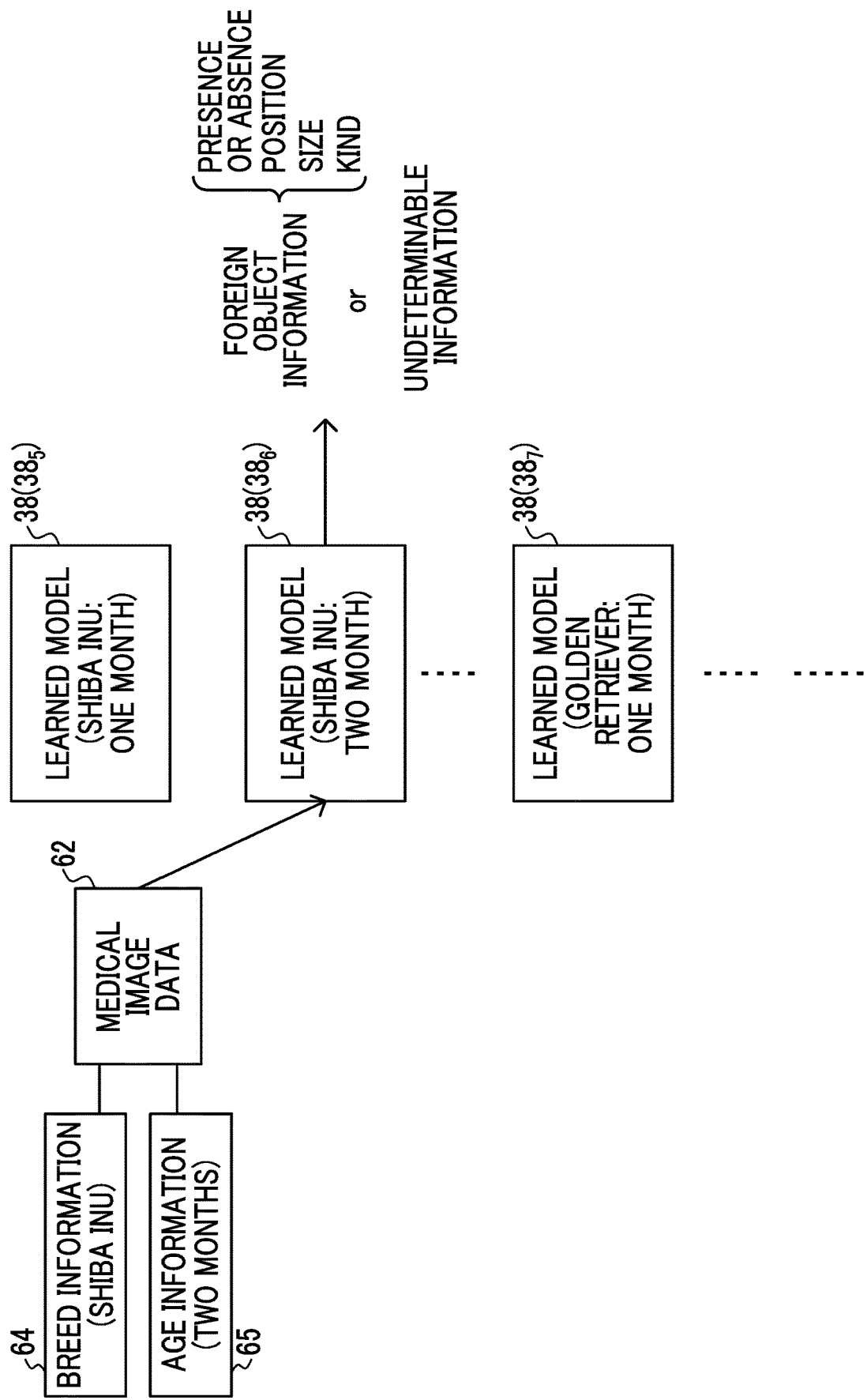

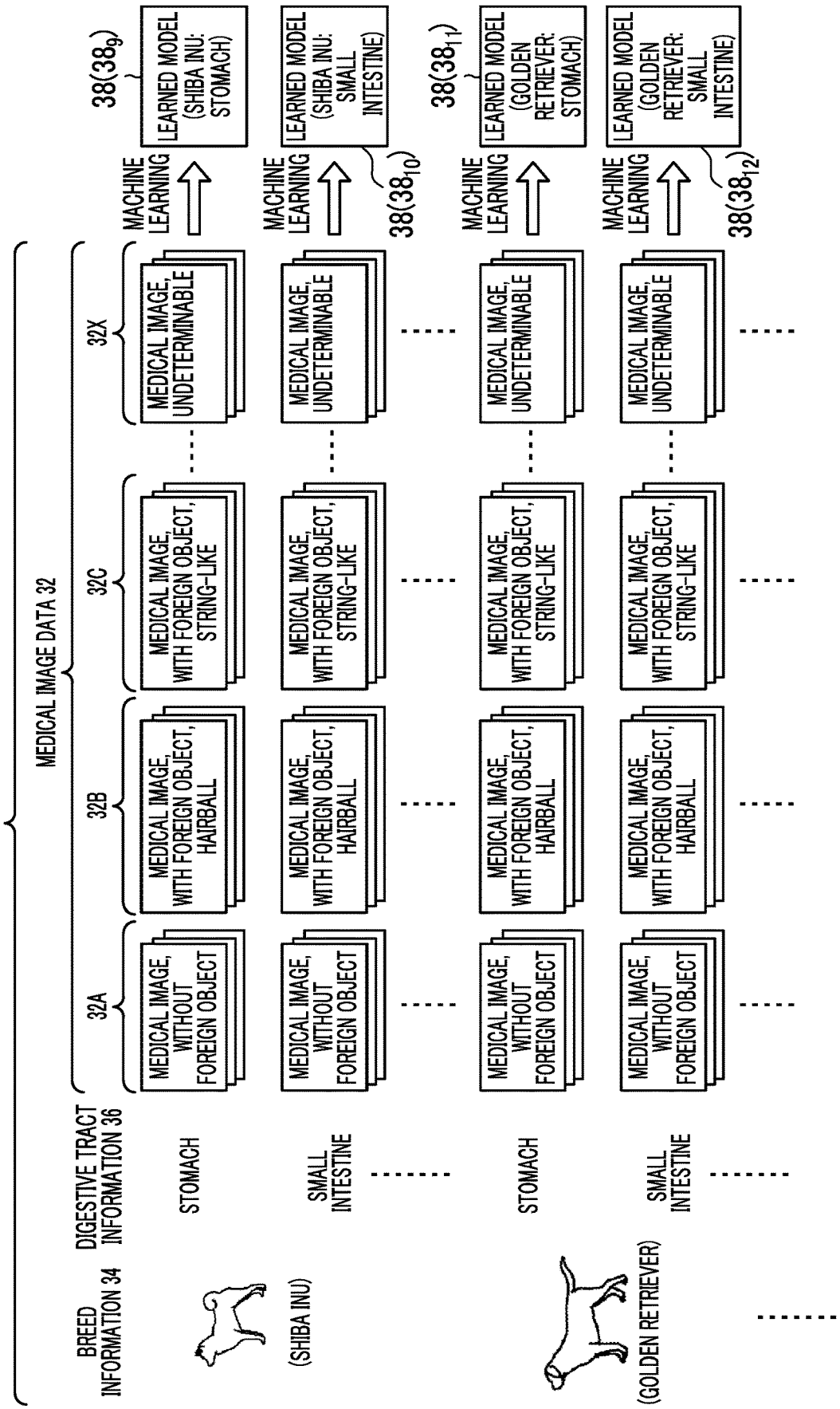

Information

MEDICAL CARE SUPPORT DEVICE, MEDICAL CARE SUPPORT METHOD, AND MEDICAL CARE SUPPORT PROGRAM

CROSS-REFERENCE TO RELATED APPLICATION

This application claims priority from Japanese Patent Application No. 2019-182723, filed Oct. 3, 2019, the disclosure of which is incorporated herein by reference in its entirety.

BACKGROUND

Technical Field

The present disclosure relates to a medical care support device, a medical care support method, and a medical care support program storage medium.

Related Art

In general, a foreign object in a body of a subject is detected from a medical image of the subject. For example, JP2017-202310A discloses a technique of detecting a foreign object such as a metal in a subject, which is an obstacle to diagnosis.

By the way, there is a foreign object that is required to be removed from the body of the subject as the foreign object in the body of the subject. For example, in a case where the subject is an animal such as a dog, a swallowed hairball due to grooming, a string-like object, or the like may be present in a digestive tract as the foreign object. However, this type of foreign object needs to be removed. In particular, there is a case where a position or the like of the foreign object in the digestive tract changes over time. Therefore, it is desired to support medical care for removing the foreign object from the body of the subject.

However, although the technique described in JP2017-202310A detects the foreign object in the body of the subject, it may not be sufficient to deal with the removal of the detected foreign object.

SUMMARY

The present disclosure has been made in view of the above circumstances, and a purpose thereof is to provide a medical care support device, a medical care support method, and a medical care support program storage medium capable of effectively supporting medical care related to a removal of a foreign object in a digestive tract of a subject.

A medical care support device according to a first aspect of the present disclosure comprises an acquisition unit that acquires medical information including medical image data representing a medical image obtained by capturing a digestive tract of a subject, a derivation unit that derives presence or absence of a foreign object in the digestive tract of the subject, based on the medical information acquired by the acquisition unit and a learned model learned in advance using a plurality of pieces of learning medical information including the medical image data in which a label according to a kind of the foreign object is assigned to the foreign object in the digestive tract according to each organ of the digestive tract, and derives at least one of position, size, or kind of the foreign object in a case where the foreign object is present, and an output unit that outputs removal information representing a predetermined removal method of the foreign object according to the at least one of position, size, or kind of the foreign object in a case where the foreign object is present, based on a result of the derivation of the derivation unit.

In the medical care support device according to a second aspect of the present disclosure, the medical information further includes breed information representing a breed of the subject, and the learning medical information further includes the breed information, in the medical care support device according to the first aspect.

In the medical care support device according to a third aspect of the present disclosure, the medical information further includes body type information representing a kind relating to a body type of the subject, and the learning medical information further includes the body type information, in the medical care support device according to the first aspect.

In the medical care support device according to a fourth aspect of the present disclosure, the medical information further includes age information representing an age of the subject, and the learning medical information further includes the age information, in the medical care support device according to any one of the first to third aspects.

In the medical care support device according to a fifth aspect of the present disclosure, a plurality of pieces of the learning medical information used for learning of the learned model further include learning medical information including medical image data to which a label representing that determination related to the foreign object is impossible is assigned, and the derivation unit further derives that determination related to the foreign object in the digestive tract of the subject is impossible based on the medical information acquired by the acquisition unit and the learned model, in the medical care support device according to any one of the first to fourth aspects.

In the medical care support device according to a sixth aspect of the present disclosure, the output unit outputs examination item information representing a predetermined examination item in a case where the derivation unit derives that the determination is impossible, in the medical care support device according to the fifth aspect.

In the medical care support device of a seventh aspect of the present disclosure, the foreign object is a non-lesion, in the medical care support device according to any one of the first to sixth aspects.

A medical care support method according to an eighth aspect of the present disclosure executed by a computer comprises acquiring medical information including medical image data representing a medical image obtained by capturing a digestive tract of a subject, deriving presence or absence of a foreign object in the digestive tract of the subject based on the acquired medical information and a learned model learned in advance using a plurality of pieces of learning medical information including the medical image data in which a label according to a kind of the foreign object is assigned to the foreign object in the digestive tract according to each organ of the digestive tract, deriving at least one of position, size, or kind of the foreign object in a case where the foreign object is present, and outputting removal information representing a predetermined removal method of the foreign object according to the at least one of position, size, or kind of the foreign object in a case where the foreign object is present, based on a result of the derivation.

A non-transitory storage medium according to a ninth aspect of the present disclosure stores a program that causes a computer to execute medical care support processing, the processing includes: acquiring medical information including medical image data representing a medical image obtained by capturing a digestive tract of a subject, deriving presence or absence of a foreign object in the digestive tract of the subject based on the acquired medical information and a learned model learned in advance using a plurality of pieces of learning medical information including the medical image data in which a label according to a kind of the foreign object is assigned to the foreign object in the digestive tract according to each organ of the digestive tract, deriving at least one of position, size, or kind of the foreign object in a case where the foreign object is present, and outputting removal information representing a predetermined removal method of the foreign object according to the at least one of position, size, or kind of the foreign object in a case where the foreign object is present, based on a result of the derivation.

The medical care support device according to the present disclosure comprises a memory that stores a command to be executed by a computer, and a processor configured to execute the stored command. The processor acquires medical information including medical image data representing a medical image obtained by capturing a digestive tract of a subject, derives presence or absence of a foreign object in the digestive tract of the subject based on the acquired medical information and a learned model learned in advance using a plurality of pieces of learning medical information including the medical image data in which a label according to a kind of the foreign object is assigned to the foreign object in the digestive tract according to each organ of the digestive tract, derives at least one of position, size, or kind of the foreign object in a case where the foreign object is present, and outputs removal information representing a predetermined removal method of the foreign object according to the at least one of position, size, or kind of the foreign object in a case where the foreign object is present, based on a result of the derivation.

According to the present disclosure, it is possible to effectively support the medical care related to the removal of the foreign object in the digestive tract of a subject.

BRIEF DESCRIPTION OF THE DRAWINGS

FIG. 1 is a block diagram showing an example of a configuration of a medical care support system according to a first embodiment.

FIG. 2 is a block diagram showing an example of a hardware configuration of a medical care support device according to the first embodiment.

FIG. 3 is a diagram for describing an example of learning medical information according to the first embodiment.

FIG. 5 is a diagram for describing a learned model according to the first embodiment.

FIG. 6 is a table for describing an example of removal method information.

FIG. 16A is a table for describing an example of removal method information for a small dog.

FIG. 16B is a table for describing an example of removal method information for a large dog.

FIG. 17 is a diagram for describing an input and an output of the learned model according to the second embodiment.

FIG. 21 is a diagram for describing an example of the learning medical information according to the third embodiment.

FIG. 25 is a diagram for describing derivation of foreign object information or undeterminable information using the learned model according to a combination of a dog breed and an age in the medical care support device according to the third embodiment.

FIG. 26 is a diagram for describing a learned model learned by learning medical information including age information.

DETAILED DESCRIPTION

Figure 4A:
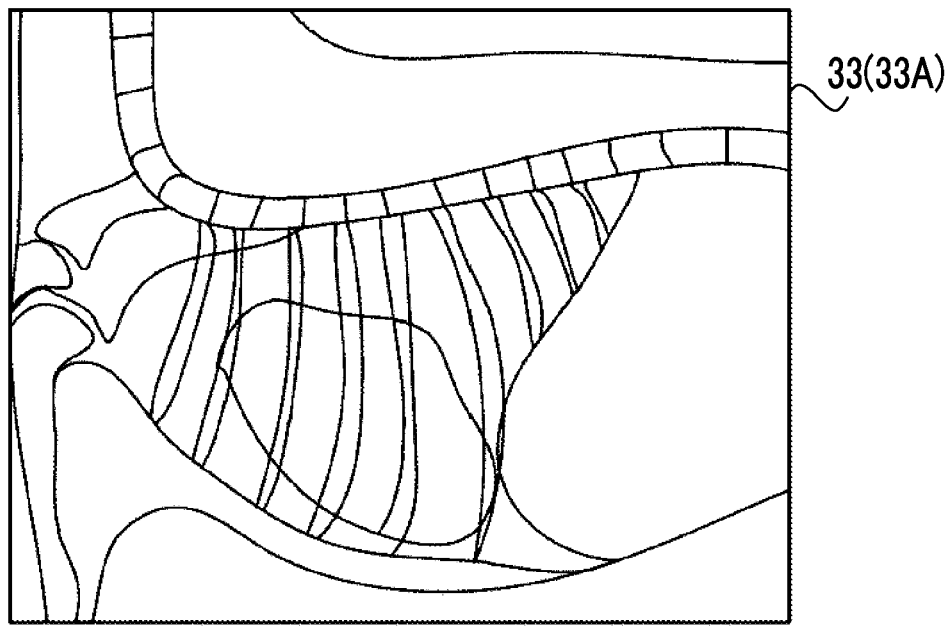
FIG. 4A is a diagram showing an example of a medical image captured in a state where a foreign object is not included in a digestive tract.

Hereinafter, an embodiment for implementing a technique of the present disclosure will be described in detail with reference to drawings. In the following embodiment, a case where a "dog" is employed as a subject will be described.

First Embodiment

First, a medical care support system 1 according to the present embodiment will be described with reference to FIG. 1. FIG. 1 is a block diagram representing an example of a configuration of the medical care support system 1 according to the present embodiment. As shown in FIG. 1, the medical care support system 1 according to the present embodiment comprises a medical care support device 10 and a plurality (three in FIG. 1 as an example) of terminal devices 12. The medical care support device 10 and the plurality of terminal devices 12 are respectively connected to a network N and can communicate with each other through the network N.

The medical care support device 10 is installed in, for example, an animal hospital. An example of the medical care support device 10 includes a server computer. The medical care support device 10 may be a cloud server. The terminal device 12 is installed in, for example, the animal hospital and used by a user such as a veterinarian. Examples of the terminal device 12 include a personal computer and a tablet computer.

Next, an example of a hardware configuration of the medical care support device 10 according to the present embodiment will be described with reference to FIG. 2. As shown in FIG. 2, the medical care support device 10 includes a central processing unit (CPU) 20, a memory 21 as a temporary storage area, and a nonvolatile storage unit 22. The medical care support device 10 includes a display unit 24 such as a liquid crystal display, an input unit 26 such as a keyboard or a mouse, and a network interface (I/F) 28 connected to the network N. The display unit 24 and the input unit 26 may be integrated as a touch panel display. The CPU 20, the memory 21, the storage unit 22, the display unit 24, the input unit 26, and the network I/F 28 are connected to a bus 29 communicably with each other.

The storage unit 22 is formed by a hard disk drive (HDD), a solid state drive (SSD), a flash memory, and the like. The storage unit 22 as a storage medium stores a learning program 23A. The CPU 20 reads out the learning program 23A from the storage unit 22, develops the program in the memory 21, and executes the developed learning program 23A. The storage unit 22 stores a medical care support program 23B. The CPU 20 reads out the medical care support program 23B from the storage unit 22, develops the program in the memory 21, and executes the developed medical care support program 23B.

The storage unit 22 according to the present embodiment stores learning medical information 30 and a learned model 38 learned using the learning medical information 30.

As shown in FIGS. 2 and 3, the learning medical information 30 according to the present embodiment includes medical image data 32, breed information 34, and digestive tract information 36 for learning, as an example.

In a case where a foreign object is present in a digestive tract for a medical image obtained by capturing a portion including a digestive tract of the dog which is the subject using the medical image capturing device, the medical image data 32 is image data representing a medical image 33 in which a label (details will be described below) is assigned to the foreign object. In the present embodiment, an embodiment of employing a radiographic image according to a radiation amount detected by a radiation detector that irradiates the dog of the subject with radiation and detects radiation transmitted through the dog will be described as the medical image. The medical image may be a medical image obtained by being captured in a state where a contrast medium is administered, a magnetic resonance imaging (MRI) image, a computed tomography (CT) image, and the like.

An example of the medical image 33 according to the present embodiment will be described with reference to FIGS. 4A to 4E. The medical images 33 (33A to 33C, 33X) shown in FIGS. 4A to 4D are medical images obtained by capturing a portion including the stomach, which is the digestive tract of the dog, in a side surface direction (so-called Lateral).

FIG. 4A shows a medical image 33A captured in a state where a foreign object is not included in the digestive tract. No shadow due to the foreign object is viewed in the digestive tract appearing in the medical image 33A.

Figure 4B:
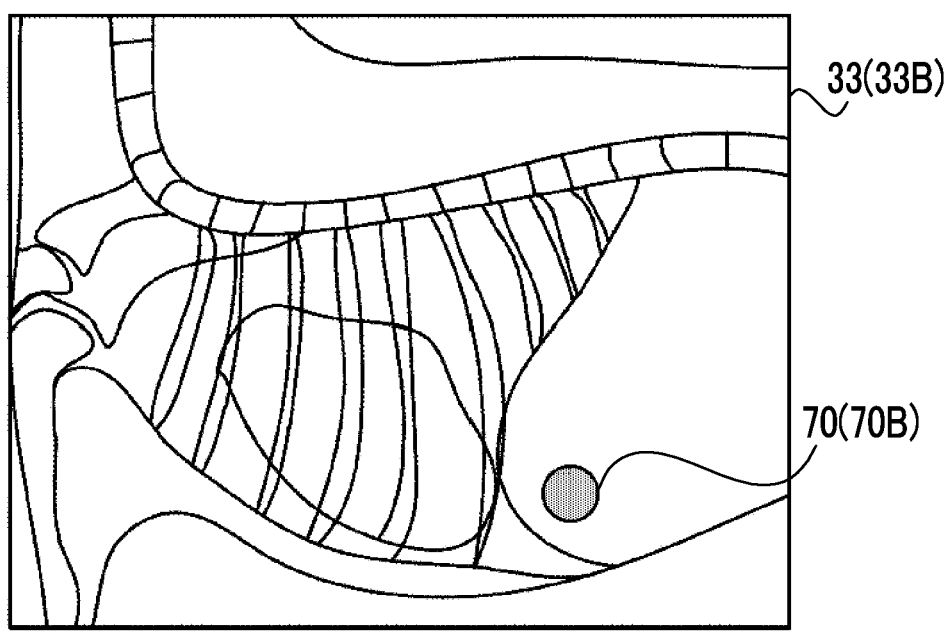
FIG. 4B is a diagram showing an example of a medical image in which a foreign object label is assigned to a foreign object included in the digestive tract.
Figure 4C:
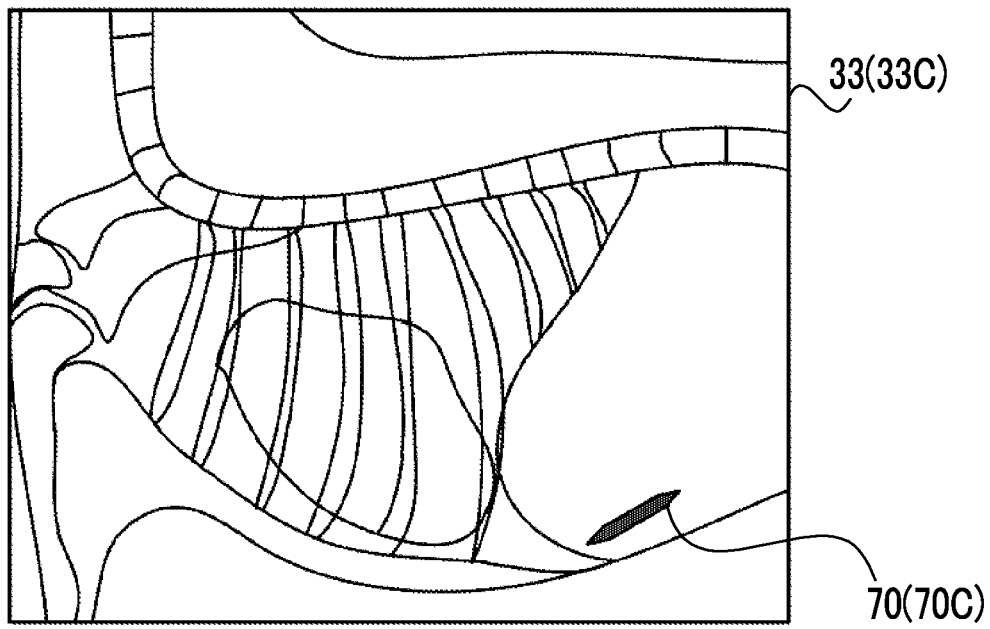
FIG. 4C is a diagram showing an example of a medical image in which a foreign object label is assigned to a foreign object included in the digestive tract.

FIG. 4B shows a medical image 33B in which a label (hereinafter referred to as "foreign object label") 70B is assigned to a foreign object included in the digestive tract. FIG. 4C shows a medical image 33C in which a foreign object label 70C is assigned to a foreign object included in the digestive tract. The medical images 33B and 33C are medical images captured in a state where the digestive tract includes the foreign object, and the foreign object labels 70B and 70C are respectively assigned to the shadows of the foreign objects.

A foreign object is an object that is not originally present or is not required to be present in a body of the subject. As an example, the foreign object according to the present embodiment is a non-lesion and is an object invaded into the body of the subject, specifically, the digestive tract due to accidental ingestion by the subject or the like. Examples of the foreign object include various things such as a stone, a string, a toy, a skewer, a coin, and a cloth. In a case where the subject is an animal such as the dog as in the present embodiment, an example of the foreign object includes a hair (hairball) of the dog due to grooming. As described above, there are various kinds of foreign objects and various kinds of materials thereof. In this embodiment, the foreign object label 70 is assigned to the shadow of the foreign object in the medical image according to the kind of the foreign object.

The "kind" of the foreign object is not limited to a kind representing a specific object such as stone, string, or hairball, and may be a kind according to a shape in a case where the shape is classified, such as a circle, a string, or a protrusion. In the present embodiment, the subject is the dog and there are various kinds of specific objects to be accidentally ingested. Therefore, in a case where the foreign object labels 70 is assigned according to the kind of the specific object such as "stone", the number of kinds of foreign object labels 70 will be enormous. In a case where an unexpected foreign object is accidentally ingested, there is a concern that there is no foreign object label 70 required to be assigned to the unexpected foreign object. In the present embodiment, the kind of foreign object is not the kind of the specific object, but the kind according to the shape. For example, the foreign object label 70B shown in FIG. 4B is the foreign object label 70 assigned to a circular foreign object. For example, the foreign object label 70C shown in FIG. 4C is the foreign object label 70 assigned to a skewer-like foreign object.

Figure 4D:
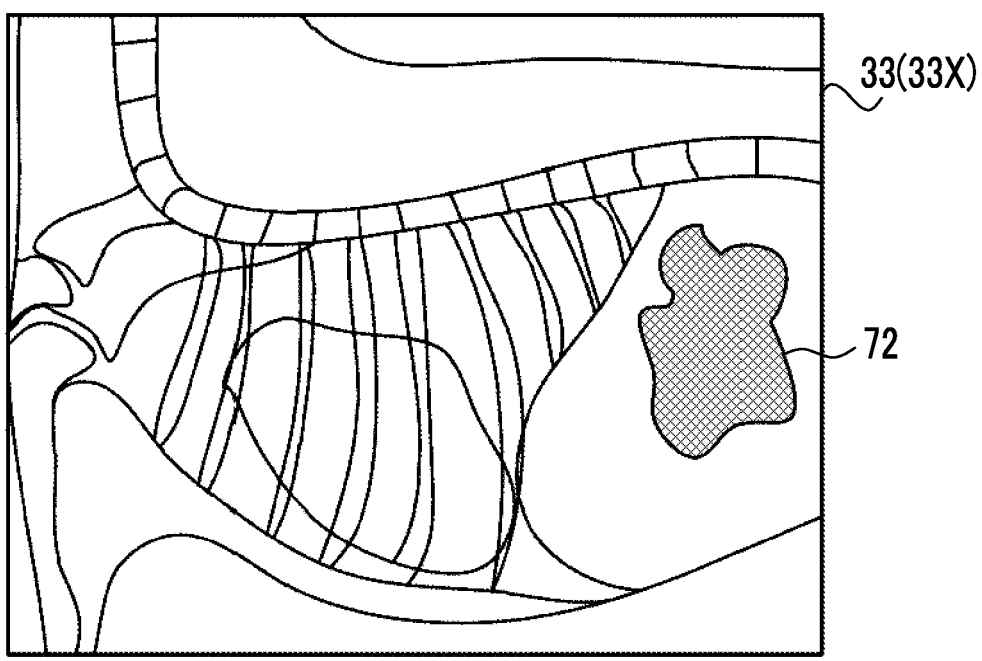
FIG. 4D is a diagram showing an example of a medical image in which an undeterminable label is assigned to a shadow included in the digestive tract.

In the medical image obtained by capturing the digestive tract of the subject, there is a case where there is a shadow finding due to a possibility that there is a shadow due to the foreign object, or the like, but it is impossible to determine whether the shadow is due to the foreign object. There is a case where it is impossible to determine a position, a size, and a kind of the foreign object since the shadow due to the foreign object is a shadow of another portion, or the like. In the present embodiment, for the shadow in the medical image 33 in which the digestive tract is captured, an undeterminable label 72 is assigned to a shadow that cannot be determined to be a lesion and in which the foreign object in the digestive tract cannot be determined, specifically, at least one of position, size, or kind of the foreign object is unable to be determined, as shown in FIG. 4D. FIG. 4D shows a medical image 33X to which the undeterminable label 72 is assigned.

Figure 4E:
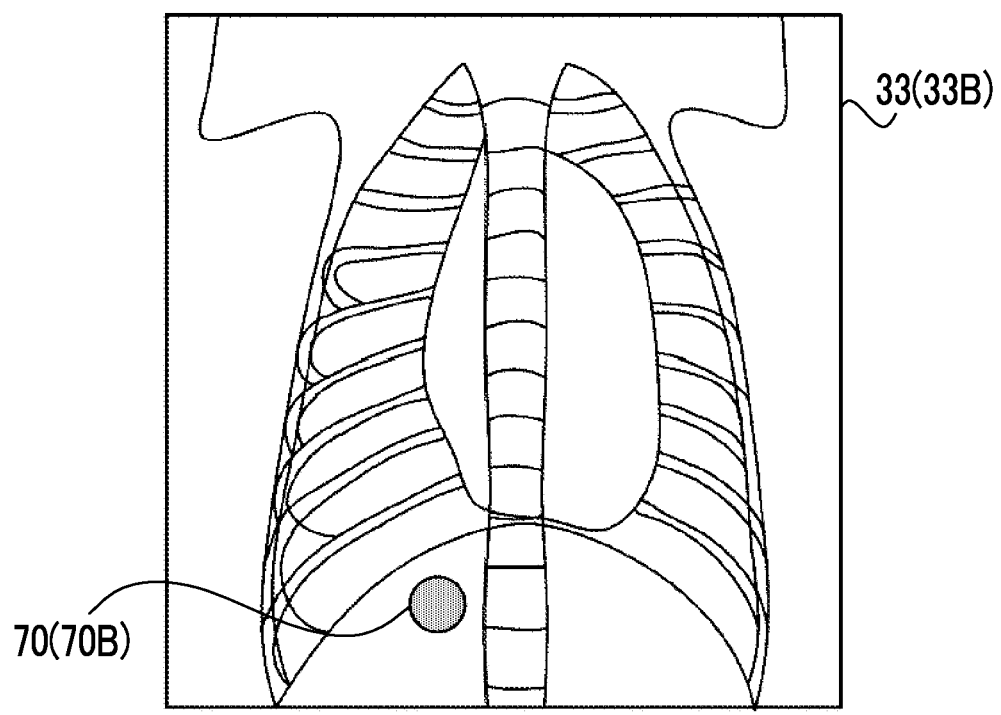
FIG. 4E is a diagram showing another example of the medical image in which the foreign object label is assigned to the foreign object included in the digestive tract.

The medical image may be, for example, the medical image 33B obtained by capturing in a direction from an abdominal side to a back side (so-called Ventral-Dorsal) as shown in FIG. 4E. The medical image 33B shown in FIG. 4E is a medical image in which the digestive tract with the assigned foreign object label 70B is captured. In a case where a plurality of medical image data 32 used as the learning medical information 30 include the medical image data 32 based on the medical images 33 having different imaging directions, it is preferable to assign information representing the imaging direction to the medical image data 32.

As described above, the medical image data 32 according to the present embodiment includes a plurality of pieces of medical image data 32A representing the medical image 33A in which no shadow of the foreign object is viewed in the digestive tract, in other words, to which the foreign object label 70 is not assigned, a plurality of pieces of medical image data 32B and 32C representing the medical images 33B and C to which the foreign object label 70 is assigned, and a plurality of pieces of medical image data 32X representing the medical image 33X to which the undeterminable label 72 is assigned, respectively.

The breed information 34 is breed information representing a breed of the dog which is the subject and is added to the medical image data 32. Specifically, the breed information 34 is information representing a dog breed since the subject is the dog. In the present embodiment, the "breed" includes a concept of species such as "dog" and "cat" in addition to the breed such as "dog breed".

The digestive tract information 36 is information representing the digestive tract in which the shadow of the foreign object is present. Examples of the digestive tract in which the foreign object is present include the stomach, a small intestine, and a large intestine, and the digestive tract information 36 is information representing the portions of the digestive tracts.

The learned model 38 is a model learned in advance using the learning medical information 30. In the present embodiment, the learned model 38 is generated by machine learning using the learning medical information 30 as shown in FIG. 5 as an example. For example, as shown in FIG. 5, in a case where the dog breed represented by the breed information 34 is "Shiba Inu", a learned model $38_1$ for which the dog breed is Shiba Inu is generated, from the medical image data 32A to 32C and 32X in which the digestive tract represented by the digestive tract information 36 is "stomach" and the medical image data 32A to 32C and 32X in which the digestive tract represented by the digestive tract information 36 is "small intestine".

For example, as shown in FIG. 5, in a case where the dog breed represented by the breed information 34 is "Golden Retriever", a learned model $38_2$ for which the dog breed is Golden Retriever is generated, from the medical image data 32A to 32C and 32X in which the digestive tract represented by the digestive tract information 36 is "stomach" and the medical image data 32A to 32C and 32X in which the digestive tract represented by the digestive tract information 36 is "small intestine". An example of the learned model 38 includes a neural network model.

FIG. 5 shows the learned models $38_1$ to $38_2$ in the case where the dog breeds are "Shiba Inu" and "Golden Retriever" and the digestive tracts are "stomach" and "small intestine". However, the kinds of the dog breed and the digestive tract are not limited thereto. In a case where the learned models $38_1$ and $38_2$ are collectively referred to without distinction, the symbols "1" and "2" for distinguishing the individual models are omitted and the models are referred to as "learned model 38".

As shown in FIG. 2, removal method information 40 is stored in the storage unit 22 according to the present embodiment. The removal method information 40 is information representing a correspondence relationship between the position, size, and kind of the foreign object in the digestive tract and a removal method of the foreign object. FIG. 6 shows an example of the removal method information 40.

Examples of the removal method of the foreign object include administration of an emetic agent, removal by an endoscope, laparotomy, administration of a laxative, and follow-up observation for spontaneous elimination. The removal method of the foreign object differs depending on the position, size, kind, and the like of the foreign object. For example, in a case where the position of the foreign object is in the stomach, the size thereof is relatively small, and the shape thereof is circular or the like and is less likely to damage an internal organ (digestive organ), the removal method by the administration of the emetic agent tends to be adopted. For example, in a case where the position of the foreign object is the small intestine and the shape thereof is a string, the intestine may be in a so-called accordion state regardless of the size of the foreign object. Therefore, the removal method by the laparotomy tends to be adopted. As described above, the removal method of the foreign object differs depending on at least one of the position, size, or kind of foreign object. Therefore, the information representing the correspondence relationship between the position, size, and kind of the foreign object in the digestive tract and the removal method of the foreign object is stored in the storage unit 22 as the removal method information 40. The removal method information 40 is not limited to the present embodiment and may be any information representing the correspondence relationship between at least one of the position, size, or kind of the foreign object and the removal information of the foreign object.

Examination item information 42 is stored in the storage unit 22 according to the present embodiment. The examination item information 42 is information representing an examination item recommended to be performed on the subject in order to determine (specify) the shadow, in a case where a shadow in the medical image is the undeterminable shadow as described above. Examples of the examination item include performing of different kinds of imaging such as imaging of an ultrasound image or imaging of a CT image, in a case where the medical image is a radiographic image.

Figure 7:
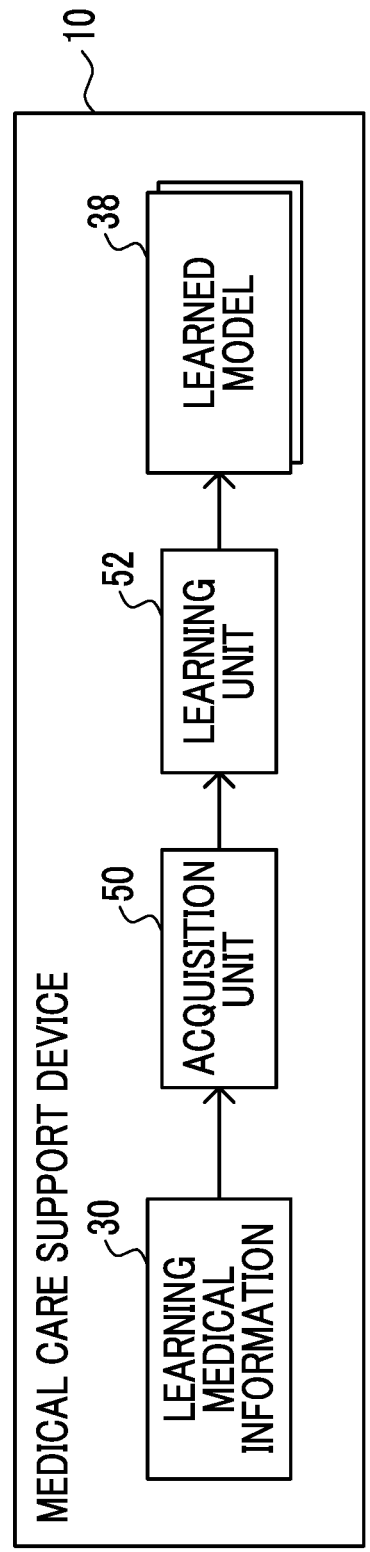
FIG. 7 is a block diagram showing an example of a functional configuration of the medical care support device according to the first embodiment in a learning phase.

Next, a functional configuration of the medical care support device 10 according to the present embodiment in a learning phase will be described with reference to FIG. 7. As shown in FIG. 7, the medical care support device 10 includes an acquisition unit 50 and a learning unit 52. The CPU 20 executes the learning program 23A to function as the acquisition unit 50 and the learning unit 52.

The acquisition unit 50 acquires the learning medical information 30 from the storage unit 22.

The learning unit 52 performs learning of the learning medical information 30 acquired by the acquisition unit 50 as learning data (also referred to as teacher data) to generate the learned model 38 that outputs information on the foreign object (hereinafter referred to as "information on foreign object") or information representing that determination is impossible (hereinafter referred to as "undeterminable information") based on the learning medical information 30. Specifically, the learning unit 52 generates, by machine learning, a plurality of learned models 38 according to the breed that receive the medical image data 32 to which the digestive tract information 36 is assigned and output the foreign object information or the undeterminable information in the medical image 33 represented by the medical image data 32, for each dog breed represented by the breed information 34. In the present embodiment, the "foreign object information" specifically includes information on the presence or absence of the foreign object, the position of the foreign object, the size of the foreign object, and the kind of the foreign object. In the present embodiment, in a case where the foreign object is absent, specifically, in a case where the shadow due to the foreign object is absent in the digestive tract in the medical image 33, the foreign object information includes only information representing that the foreign object is absent.

In order to output the information representing the size of the foreign object from the learned model 38, the medical image 33 may include information for deriving the size of the foreign object, for example. Specifically, for example, the medical image 33 may be a medical image obtained by capturing a reference object such as a marker having a predetermined size together with the subject. For example, the learning medical information 30 may include additional information for deriving the size of the foreign object from the medical image 33. Specifically, for example, the learning medical information 30 may include information representing a size of the subject.

More specifically, in a case where the medical image data 32 to which "Shiba Inu" is added as the dog breed represented by the breed information 34 and "stomach" is added as the digestive tract represented by the digestive tract information 36 is input, the learning unit 52 causes the model to learn such that the foreign object information or the undeterminable information is output. Further, in a case where the medical image data 32 to which "Shiba Inu" is added as the dog breed represented by the breed information 34 and "small intestine" is added as the digestive tract represented by the digestive tract information 36 is input, the learning unit 52 causes the model to learn such that the foreign object information or the undeterminable information is output. With the learning, the learned model $38_1$ for which the dog breed is Shiba Inu is generated.

Similarly, in a case where the medical image data 32 to which the "Golden Retriever" is added as the dog breed represented by the breed information 34 and the "stomach" is added as the digestive tract represented by the digestive tract information 36 is input, the learning unit 52 causes the model to learn such that the foreign object information or the undeterminable information is output. In a case where the medical image data 32 to which "Golden Retriever" is added as the dog breed represented by the breed information 34 and "small intestine" is added as the digestive tract represented by the digestive tract information 36 is input, the learning unit 52 causes the model to learn such that the foreign object information or the undeterminable information is output. With the learning, the learned model $38_2$ for which the dog breed is Golden Retriever is generated.

Figure 8:
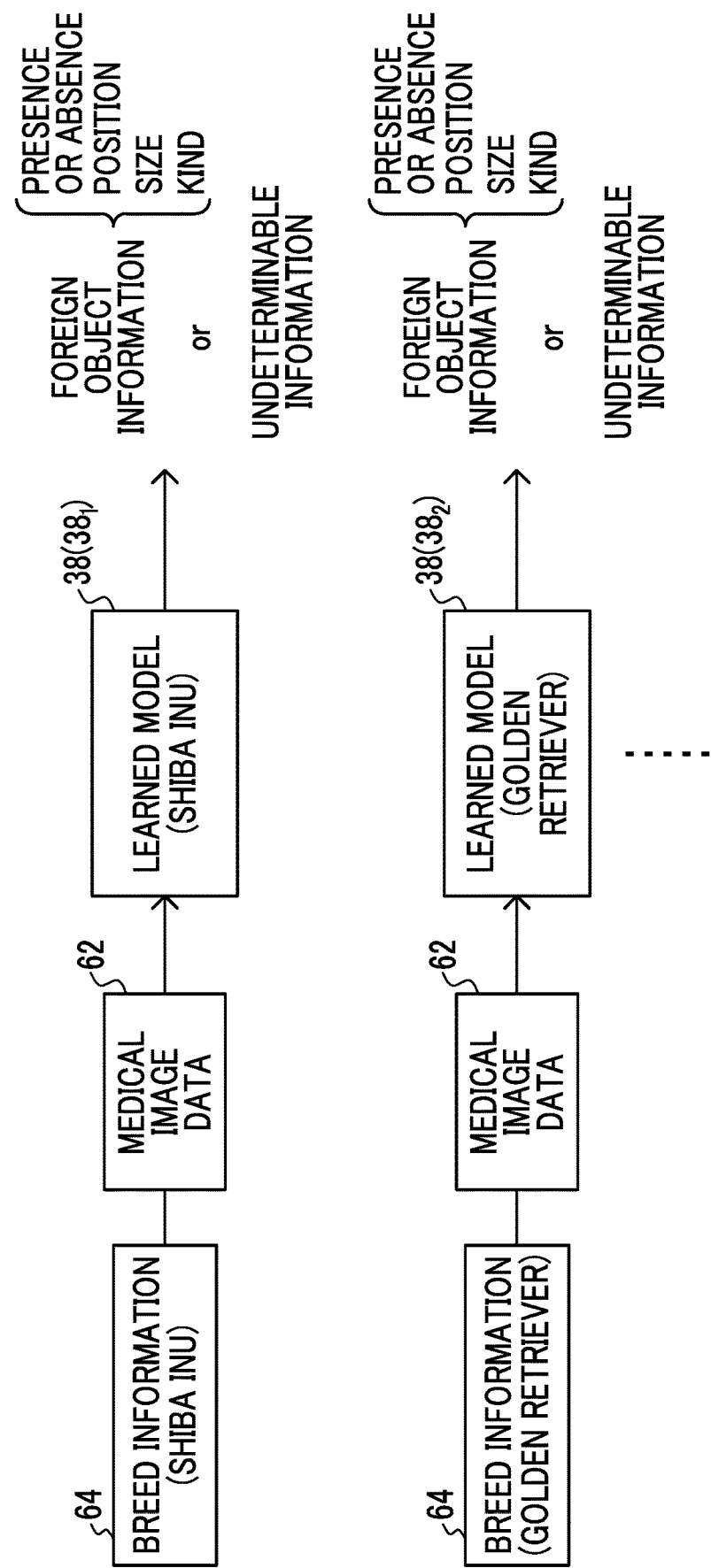
FIG. 8 is a diagram for describing an input and an output of the learned model according to the first embodiment.

For example, the error back propagation method may be employed as an algorithm of the learning by the learning unit 52 described above. As shown in FIG. 8 as an example, the learned model 38 is generated by the learning by the learning unit 52 described above, which receives the medical image data 62 and the breed information 64 and outputs the foreign object information or the undeterminable information for the foreign object in the medical image represented by the input medical image data 62, for each breed (dog breed). The learning unit 52 stores the generated learned model 38 in the storage unit 22. In the present embodiment, in a case where the medical image data 62 and the breed information 64 are collectively referred to, the information is referred to as "medical information".

Next, an action of the medical care support device 10 according to the present embodiment in the learning phase will be described with reference to FIG. 9. The CPU 20 executes the learning program 23A to execute learning processing shown in FIG. 9.

Figure 9:
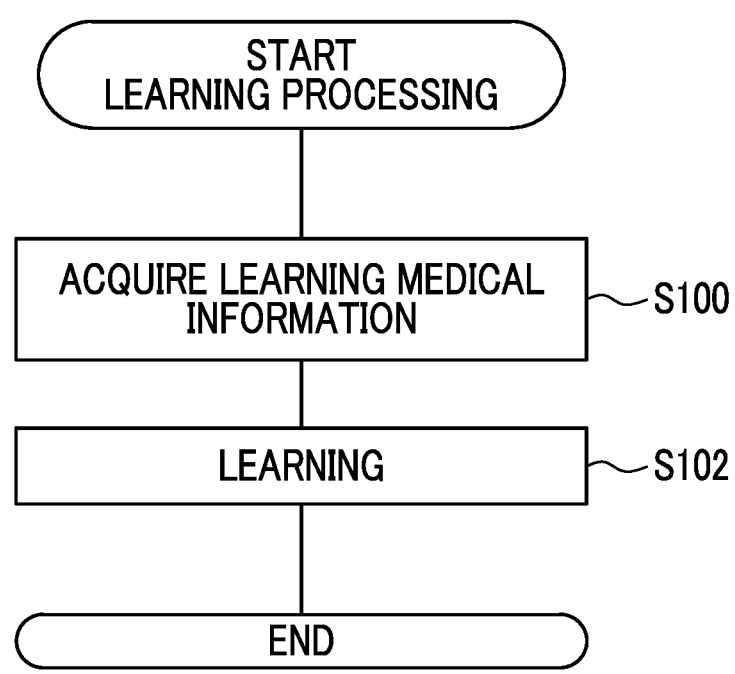
FIG. 9 is a flowchart showing an example of learning processing executed by the medical care support device according to the first embodiment.

In step S100 in FIG. 9, the acquisition unit 50 acquires the learning medical information 30 from the storage unit 22.

In next step S102, the learning unit 52 causes the model to learn for each dog breed with the learning medical information 30 acquired in step S100 as the learning data, as described above. With the learning, the learning unit 52 generates the learned model 38 that outputs the foreign object information or the undeterminable information in the digestive tract of the subject based on the medical image data 62 and the breed information 64. The learning unit 52 stores the generated learned model 38 in the storage unit 22. In a case where the processing in step S102 ends, the learning processing ends.

Figure 10:
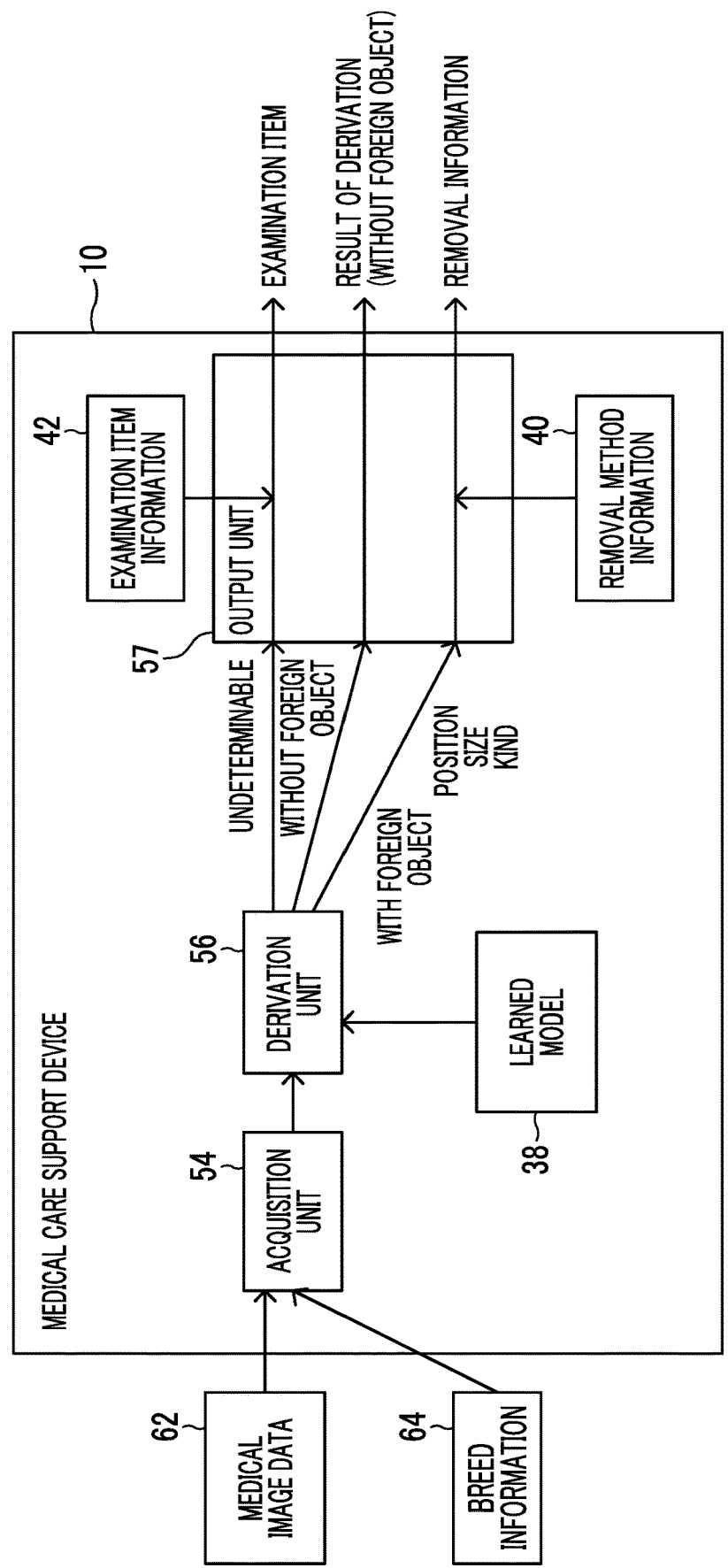
FIG. 10 is a block diagram showing an example of a functional configuration of the medical care support device according to the first embodiment in an operation phase.

Next, a functional configuration of the medical care support device 10 according to the present embodiment in the operation phase will be described with reference to FIG. 10. As shown in FIG. 10, the medical care support device 10 according to the present embodiment includes an acquisition unit 54, a derivation unit 56, and an output unit 57. The CPU 20 executes the medical care support program 23B to function as the acquisition unit 54, the derivation unit 56, and the output unit 57. The acquisition unit 54 is an example of the acquisition unit of the present disclosure, the derivation unit 56 is an example of the derivation unit of the present disclosure, and the output unit 57 is an example of the output unit of the present disclosure. The medical care support device 10 may be the same device in the learning phase and the operation phase or may be different devices.

The acquisition unit 54 acquires the medical information including the medical image data 62 representing a medical image obtained by capturing an animal of a subject which is a medical care target by the user such as the veterinarian using the medical image capturing device and the breed information 64 representing a dog breed of the subject. The breed information 64 may be added to the medical image data 62 or may be input by the user through an operation unit (not shown) of the terminal device 12.

The derivation unit 56 derives the information on the foreign object in the digestive tract of the subject based on the medical information (medical image data 62 and breed information 64) acquired by the acquisition unit 54 and the learned model 38 learned in advance by the learning medical information 30. Specifically, the derivation unit 56 inputs the medical image data 62 acquired by the acquisition unit 54 to the learned model 38 according to the dog breed represented by the breed information 64 acquired by the acquisition unit 54. The learned model 38 outputs the foreign object information or the undeterminable information according to the input medical information.

The derivation unit 56 derives whether or not the foreign object is present in the digestive tract of the subject based on the foreign object information or the undeterminable information output from the learned model 38. Specifically, in a case where the foreign object information output from the learned model 38 includes information representing that the foreign object is absent, the derivation unit 56 outputs the derivation result representing that the foreign object is absent in the digestive tract of the subject to the output unit 57. In a case where the learned model 38 derives the undeterminable information, the foreign object may actually be present in the digestive tract of the subject, but the determination is impossible. Therefore, the derivation unit 56 according to the present embodiment outputs the information representing that the determination is impossible to the output unit 57 without deriving the presence or absence of the foreign object.

In a case where the derivation unit 56 derives that the foreign object is present in the digestive tract of the subject, the output unit 57 outputs, as the derivation result, the information representing each of the position, size, and kind of the foreign object based on the foreign object information.

In a case where the derivation result representing that the foreign object is absent is input, the output unit 57 outputs the derivation result that the foreign object is absent. Specifically, in a case where the derivation result representing that the foreign object is absent is input from the derivation unit 56, the output unit 57 according to the present embodiment outputs the derivation result that the foreign object is absent to the terminal device 12 to display the derivation result on a display unit (not shown) of the terminal device 12. The user performs the medical care for the subject with reference to the derivation result displayed on the display unit of the terminal device 12. For example, the user performs the medical care for the subject assuming that the symptom of the subject is not caused by the accidental ingestion.

In a case where the derivation result representing that the foreign object is present is input, the output unit 57 refers to the removal method information 40 to acquire and output the removal method corresponding to the input information representing each of the position, size, and kind of the foreign object. Specifically, in a case where the derivation result representing that the foreign object is present is input from the derivation unit 56, the output unit 57 according to the present embodiment outputs the information (hereinafter referred to as "removal information") representing the removal method corresponding to the information representing each of the position, size, and kind of the foreign object to the terminal device 12 to display the removal information on the display unit (not shown) of the terminal device 12. The user refers to the removal information displayed on the display unit of the terminal device 12 to perform the medical care related to the removal of the foreign object in the digestive tract of the subject.

In a case where the information representing that the determination is impossible is input, the output unit 57 outputs the information representing the examination item acquired from the examination item information 42. Specifically, in a case where the information representing that the determination is impossible is input from the derivation unit 56, the output unit 57 outputs information representing a predetermined examination item to the terminal device 12 to display the examination item on the display unit (not shown) of the terminal device 12. The user refers to the examination item displayed on the display unit of the terminal device 12 to perform an additional examination or the like on the subject.

Next, an action of the medical care support device 10 according to the present embodiment in the operation phase will be described with reference to FIG. 11. The CPU 20 executes the medical care support program 23B to execute the medical care support processing shown in FIG. 11.

Figure 11:
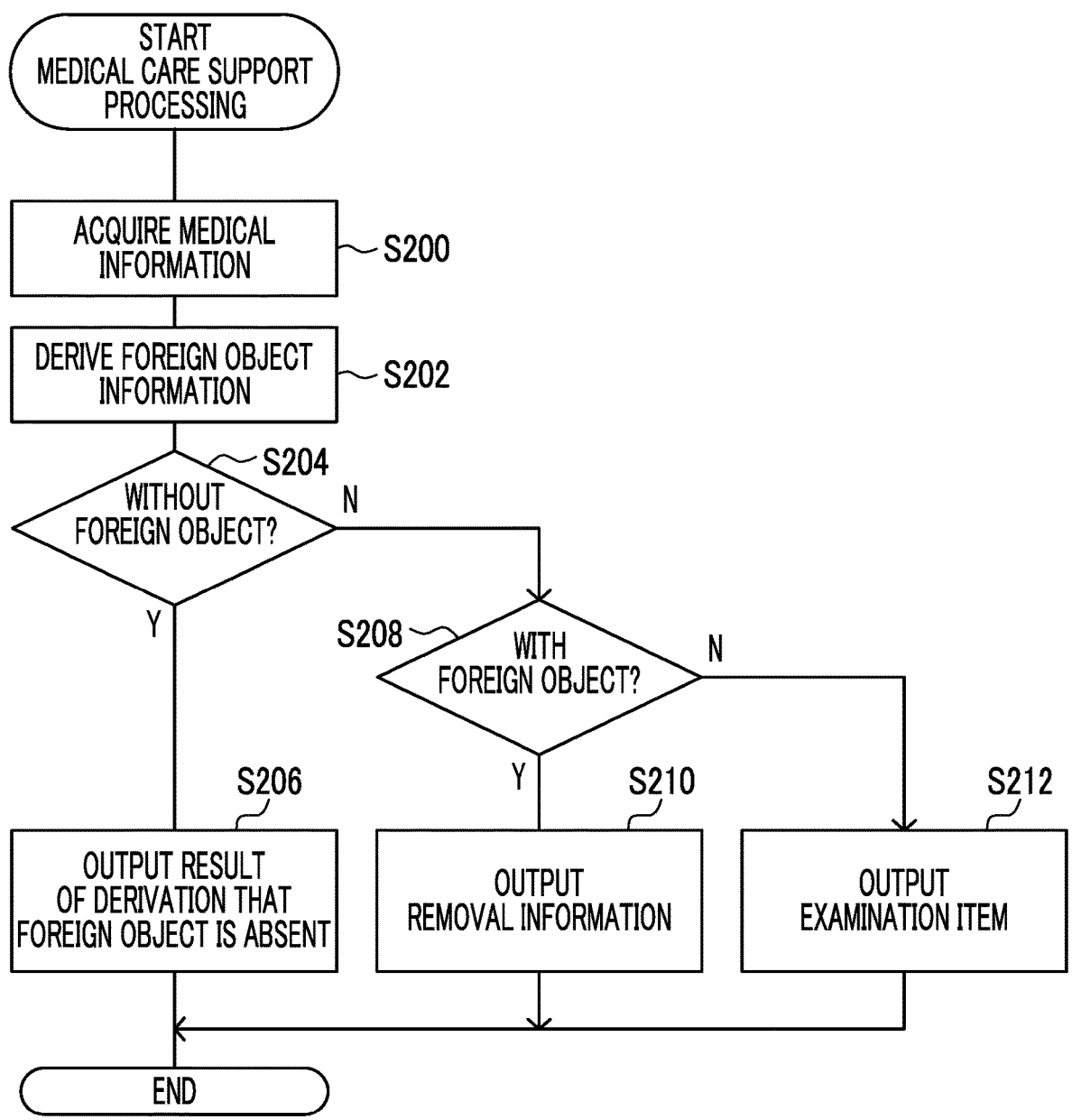
FIG. 11 is a flowchart showing an example of medical care support processing executed by the medical care support device according to the first embodiment.

In step S200 in FIG. 11, the acquisition unit 54 acquires the medical information of the dog which is the subject and outputs the medical information to the derivation unit 56. Specifically, the acquisition unit 54 acquires the medical image data 62 representing the medical image obtained by capturing the dog of the subject which is the medical care target by the user using the medical image capturing device and the breed information 64 representing the breed of the subject.

In next step S202, the derivation unit 56 derives the foreign object information based on the medical information input from the acquisition unit 54 and the learned model 38, as described above. Specifically, the derivation unit 56 inputs the medical image data 62 to the learned model 38 selected according to the breed information 64 in the input medical information to acquire the foreign object information or the undeterminable information output from the learned model 38.

Figure 12:
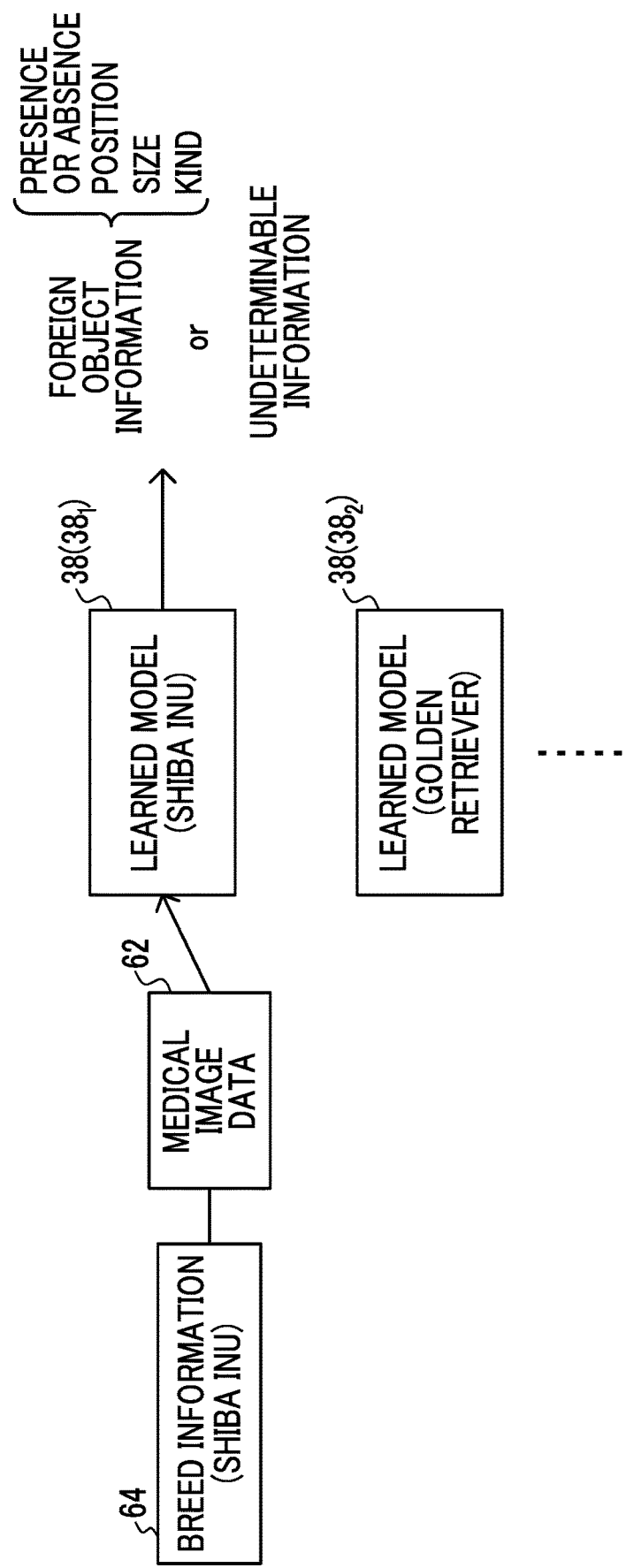
FIG. 12 is a diagram for describing derivation of foreign object information or undeterminable information using a learned model corresponding to a dog breed in the medical care support device according to the first embodiment.

For example, as shown in FIG. 12, in a case where the dog breed represented by the breed information 64 in the medical information is "Shiba Inu", the derivation unit 56 inputs the medical image data 62 to the learned model $38_1$ for which the dog breed is Shiba Inu. The foreign object information or the undeterminable information is output from the learned model $38_1$.

In next step S204, the derivation unit 56 determines whether or not the foreign object is absent in the digestive tract of the subject as described above. In a case where the learned model 38 outputs the foreign object information including the information representing that the foreign object is absent, the determination in step S204 is affirmative and the processing proceeds to step S206. In step S206, the output unit 57 outputs the derivation result that the foreign object is absent, as described above. In a case where the processing in step S206 ends, the medical care support processing ends.

On the other hand, in a case where the foreign object information output from the learned model 38 does not include the information representing that the foreign object is absent or in a case where the learned model 38 outputs the undeterminable information, the determination in step S204 is negative and the processing proceeds to step S208.

In next step S208, the derivation unit 56 determines whether or not the foreign object is present in the digestive tract of the subject as described above. In a case where the learned model 38 outputs the foreign object information representing that the foreign object is present, the determination in step S208 is affirmative and the processing proceeds to step S210. In step S210, the output unit 57 refers to the removal method information 40 as described above to acquire the removal method corresponding to the information representing each of the position, size, and kind of the foreign object input from the derivation unit 56 and output the removal information. In a case where the processing in step S210 ends, the medical care support processing ends.

On the other hand, in a case where the learned model 38 outputs the undeterminable information, the determination in step S208 is negative and the processing proceeds to step S212. In step S212, the output unit 57 outputs the examination item acquired from the examination item information 42 as described above. In a case where the processing in step S212 ends, the medical care support processing ends.

As described above, with the medical care support device 10 according to the present embodiment, the position, size, and kind of the foreign object in the digestive tract of the subject are derived based on the medical information including the medical image data 62 and the breed information 64, and the learned model 38. With the medical care support device 10 according to the present embodiment, in a case where the foreign object is present in the digestive tract of the subject, it is possible to present the removal method of the foreign object to the user.

A state of the digestive tract, a body type, or the like differs depending on the breed (dog breed) of the subject. Therefore, it is preferable to provide the removal method of the foreign object according to the breed of the subject. In the medical care support device 10 according to the present embodiment, it is possible to present the removal method of the foreign object according to the breed of the subject to the user. Therefore, it is possible to effectively support the medical care related to the removal of the foreign object in the digestive tract of the subject.

Second Embodiment

Hereinafter, a second embodiment will be described in detail.

In the present embodiment, a form will be described in which the medical care support device 10 supports the medical care related to the removal of the foreign object in the digestive tract of the subject using the medical information including the body type of the subject.

A configuration of the medical care support system 1 according to the present embodiment is the same as the configuration of the medical care support system 1 according to the first embodiment (refer to FIG. 1), and thus a description thereof will be omitted.

Figure 13:
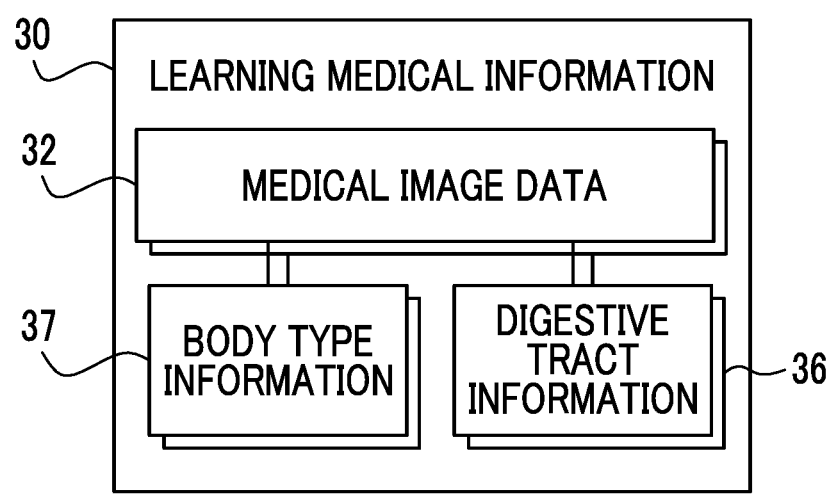
FIG. 13 is a diagram showing an example of learning medical information stored in a storage unit of a medical care support device according to a second embodiment.
Figure 14:
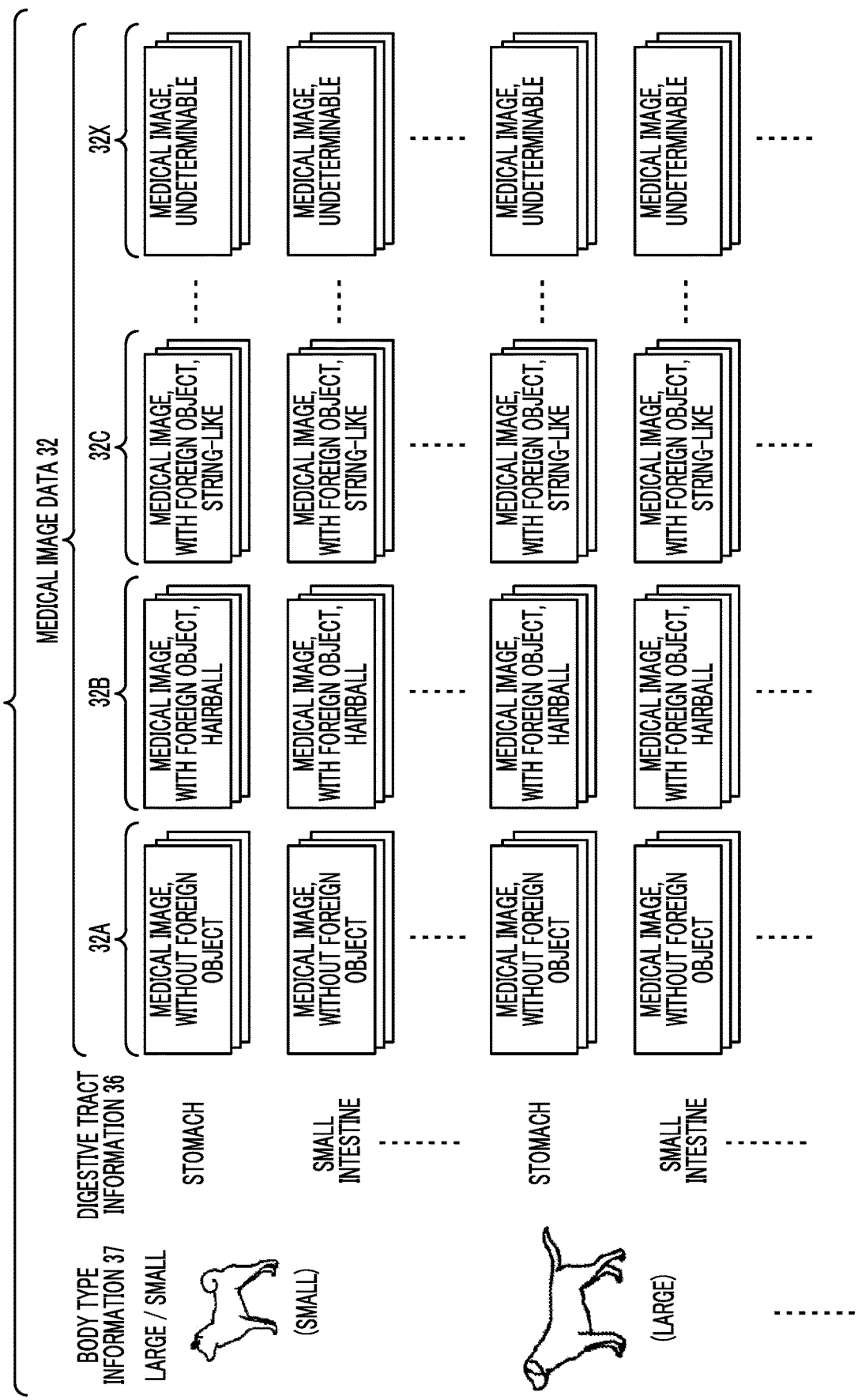
FIG. 14 is a diagram for describing an example of learning medical information according to the second embodiment.

On the other hand, in the medical care support device 10 according to the present embodiment, the contents of the medical information of the subject used for the medical care and the contents of the learning medical information 30 used for learning the learned model 38 are different from those of the first embodiment. Therefore, in the configuration of the medical care support device 10 according to the present embodiment, information included in the learning medical information 30 stored in the storage unit 22 is different from the information (refer to FIGS. 2 and 3) included in the learning medical information 30 stored in the storage unit 22 according to the first embodiment. FIGS. 13 and 14 show an example of the learning medical information 30 according to the present embodiment. As shown in FIGS. 13 and 14, the learning medical information 30 according to the present embodiment includes body type information 37 instead of the breed information 34 (refer to FIGS. 2 and 3) included in the learning medical information 30 according to the first embodiment.

The body type information 37 is information representing a kind relating to the body type of the subject. Specifically, the body type information 37 is information representing a size of the body of the subject. As an example, in the present embodiment, the information is information representing the size of the body of the subject in two stages and, specifically, is information representing whether the body type is small or large. The body type information 37 is not limited to this embodiment and may be information representing the size of the body in three or more stages such as small, medium, and large.

A method of obtaining the body type information 37 is not particularly limited. For example, a form may be employed in which the user who interprets the medical image represented by the medical image data 32 inputs the body type from an operation unit (not shown) of the terminal device 12. For example, a form may be employed in which a table representing a correspondence relationship between the dog breed and the body type is prepared in advance, the dog breed of the subject is acquired from an electronic medical record or the like, and the body type corresponding to the acquired dog breed is acquired from the table prepared in advance. For example, a form may be employed in which the body type of the subject is automatically acquired from a comparison result of comparing sizes of an examination table and the subject based on a captured image obtained by capturing the subject on the examination table with a camera or the like.

Figure 15:
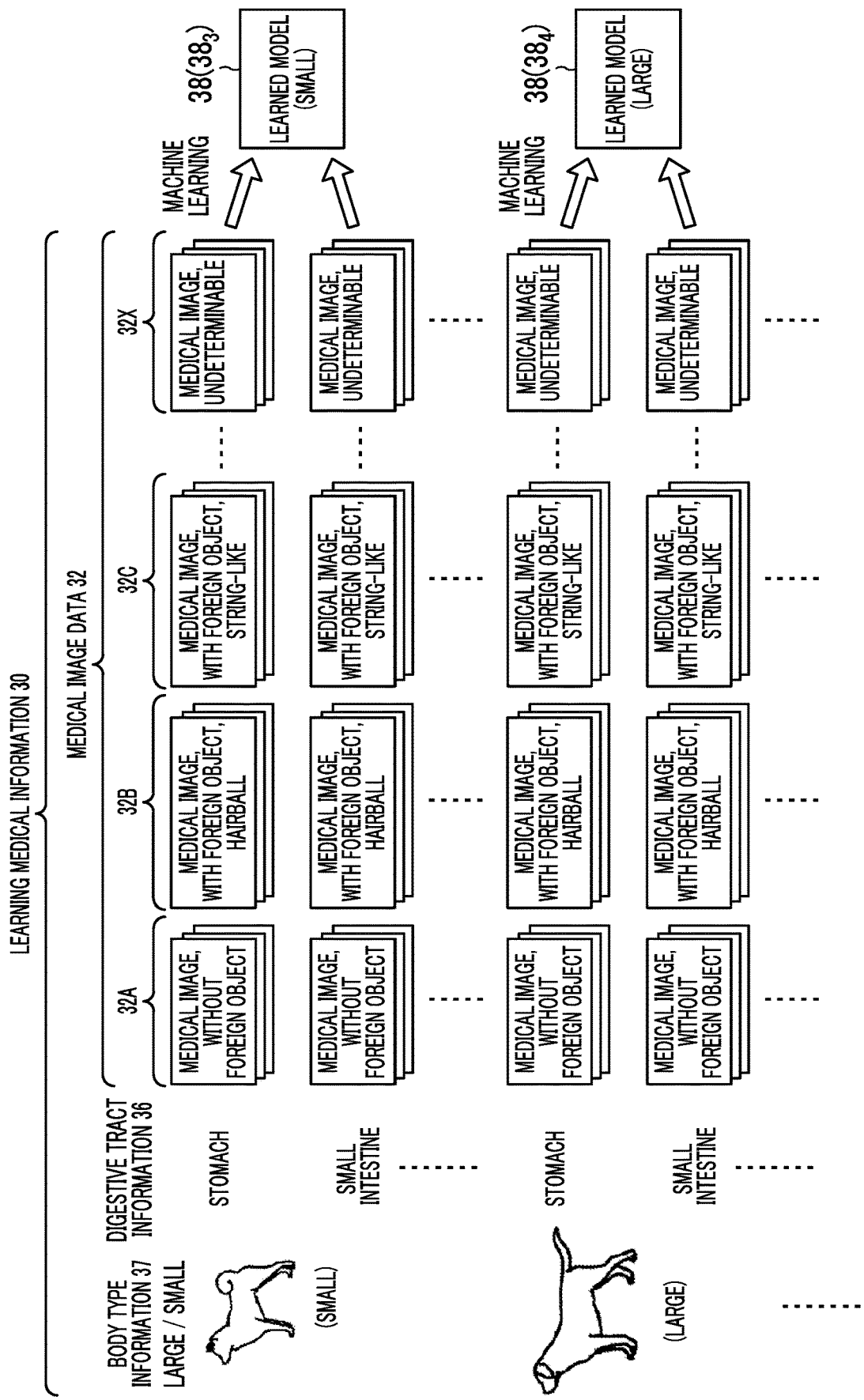
FIG. 15 is a diagram for describing a learned model according to the second embodiment.

As shown in FIG. 15, the learned model 38 according to the present embodiment is generated by machine learning using the learning medical information 30 according to the present embodiment. For example, as shown in FIG. 15, in a case where the body type represented by the body type information 37 is "small", a learned model $38_3$ for which the body type is small is generated, from the medical image data 32A to 32C and 32X in which the digestive tract represented by the digestive tract information 36 is "stomach" and the medical image data 32A to 32C and 32X in which the digestive tract represented by the digestive tract information 36 is "small intestine".

For example, as shown in FIG. 15, in a case where the body type represented by the body type information 37 is "large", a learned model $38_4$ for which the body type is large is generated, from the medical image data 32A to 32C and 32X in which the digestive tract represented by the digestive tract information 36 is "stomach" and the medical image data 32A to 32C and 32X in which the digestive tract represented by the digestive tract information 36 is "small intestine". As described above, an example of the learned model 38 includes a neural network model.

FIG. 15 shows the two learned models $38_3$ and $38_4$, the number of learned models 38 to be generated is not limited to two. In a case where the learned models $38_3$ and $38_4$ are collectively referred to without distinction, the symbols "3" and "4" for distinguishing the individual models are omitted and the models are referred to as "learned model 38".

The storage unit 22 according to the present embodiment is different in that the removal method information 40 ($40_1$ and $40_2$) shown in FIGS. 16A and 16B is stored, instead of the removal method information 40 (refer to FIGS. 2 and 6) of the first embodiment. The removal method information $40_1$ shown in FIG. 16A is removal method information 40 for a small dog, and the removal method information $40_2$ shown in FIG. 16B is removal method information 40 for a large dog. Regarding the removal method of the foreign object, it is generally said that intestinal swelling in the subject is maximum at a rib interval of the subject. Therefore, in a case where a foreign object having a size equal to or larger than the rib interval of the subject is present in the intestine, it is difficult to move the foreign object. Therefore, it is difficult to remove the foreign object with the emetic agent or the laxative, and the removal method by the laparotomy tends to be preferable. As described above, the removal method may differ depending on the size of the subject. Therefore, in the medical care support device 10 according to this embodiment, the removal method information 40 is stored in the storage unit 22 for each body type corresponding to the size of the subject.

Next, a functional configuration of the medical care support device 10 according to the present embodiment in the learning phase will be described. The overall configuration of the medical care support device 10 according to the present embodiment in the learning phase is the same as that of the medical care support device 10 according to the first embodiment (refer to FIG. 7). On the other hand, there is a difference in a specific operation of the learning unit 52 in the medical care support device 10 according to the present embodiment for generating the learned model 38 based on the learning medical information 30. Therefore, the specific operation of the learning unit 52 will be described.

The learning unit 52 according to the present embodiment generates, by machine learning, a plurality of learned models 38 according to the body type that receive the medical image data 32 and output the foreign object information or the undeterminable information in the medical image 33 represented by the medical image data 32, for each body type of the subject represented by the body type information 37.

More specifically, in a case where the medical image data 32 to which "small" is added as the body type represented by the body type information 37 is input, the learning unit 52 causes the model to learn such that the foreign object information or the undeterminable information is output. With the learning, the learned model $38_3$ for which the body type is small is generated.

Similarly, in a case where the medical image data 32 to which "large" is added as the body type represented by the body type information 37 is input, the learning unit 52 causes the model to learn such that the foreign object information or the undeterminable information is output. With the learning, the learned model $38_4$ for which the body type is large is generated.

For example, as described above, the error back propagation method may be employed as an algorithm of the learning by the learning unit 52 described above. As shown in FIG. 17 as an example, the learned model 38 is generated by the learning by the learning unit 52 described above, which receives the medical image data 62 and the body type information 67 and outputs the foreign object information or the undeterminable information for the foreign object in the medical image represented by the input medical image data 62, for each body type. The learning unit 52 stores the generated learned model 38 in the storage unit 22.

An action of the medical care support device 10 according to the present embodiment in the learning phase, that is, the learning processing executed by the medical care support device 10 is the same as the learning processing (refer to FIG. 9) executed by the medical care support device 10 according to the first embodiment, and thus the description thereof is omitted.

Figure 18:
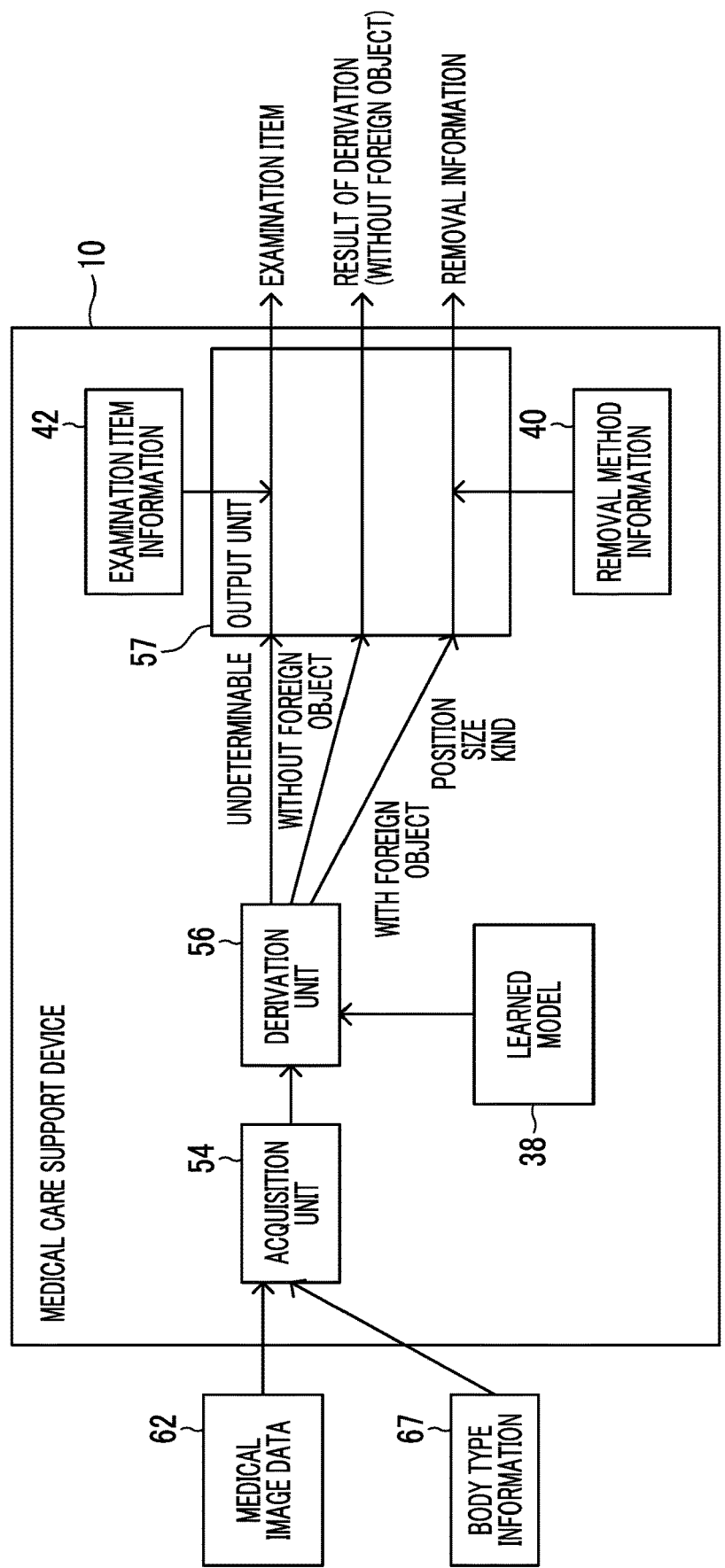
FIG. 18 is a block diagram showing an example of a functional configuration of the medical care support device according to the second embodiment in an operation phase.

Next, a functional configuration of the medical care support device 10 according to the present embodiment in the operation phase will be described with reference to FIG. 18. The medical care support device 10 according to the present embodiment differs from the medical care support device 10 (refer to FIG. 10) according to the first embodiment in specific operations of the acquisition unit 54, the derivation unit 56, and the output unit 57. Therefore, the specific operations of the acquisition unit 54, the derivation unit 56, and the output unit 57 will be described.

The acquisition unit 54 acquires the medical information including the medical image data 62 representing a medical image in which the subject is captured and the body type information 67 representing the kind relating to the body type of the subject. The body type information 67 may be added to the medical image data 62 or may be input by the user through the operation unit (not shown) of the terminal device 12.

The derivation unit 56 derives the information on the foreign object in the digestive tract of the subject based on the medical information (medical image data 62 and body type information 67) acquired by the acquisition unit 54 and the learned model 38 learned in advance by the learning medical information 30. Specifically, the derivation unit 56 inputs the medical image data 62 acquired by the acquisition unit 54 to the learned model 38 according to the body type represented by the body type information 67 acquired by the acquisition unit 54. The learned model 38 outputs the foreign object information or the undeterminable information according to the input medical information.

In a case where the derivation result representing that the foreign object is present is input from the derivation unit 56, the output unit 57 refers to the removal method information 40 ($40_1$ or $40_2$) according to the body type represented by the body type information 67 acquired by the acquisition unit 54 to acquire and output the removal method corresponding to the input information representing each of the position, size, and kind of the foreign object.

Next, an action of the medical care support device 10 according to the present embodiment in the operation phase will be described. The overall flow of the medical care support processing is the same as the medical care support processing shown in FIG. 11 according to the first embodiment and thus will be described with reference to FIG. 11.

In step S200, the acquisition unit 54 acquires the medical information of the dog which is the subject and outputs the medical information to the derivation unit 56. Specifically, the acquisition unit 54 acquires the medical image data 62 representing the medical image obtained by capturing the dog of the subject which is the medical care target by the user using the medical image capturing device and the body type information 67 representing the kind relating to the body type of the subject.

In next step S202, the derivation unit 56 derives the foreign object information based on the medical information input from the acquisition unit 54 and the learned model 38, as described above. Specifically, the derivation unit 56 inputs the medical image data 62 to the learned model 38 selected according to the body type information 67 in the input medical information to acquire the foreign object information or the undeterminable information output from the learned model 38.

Figure 19:
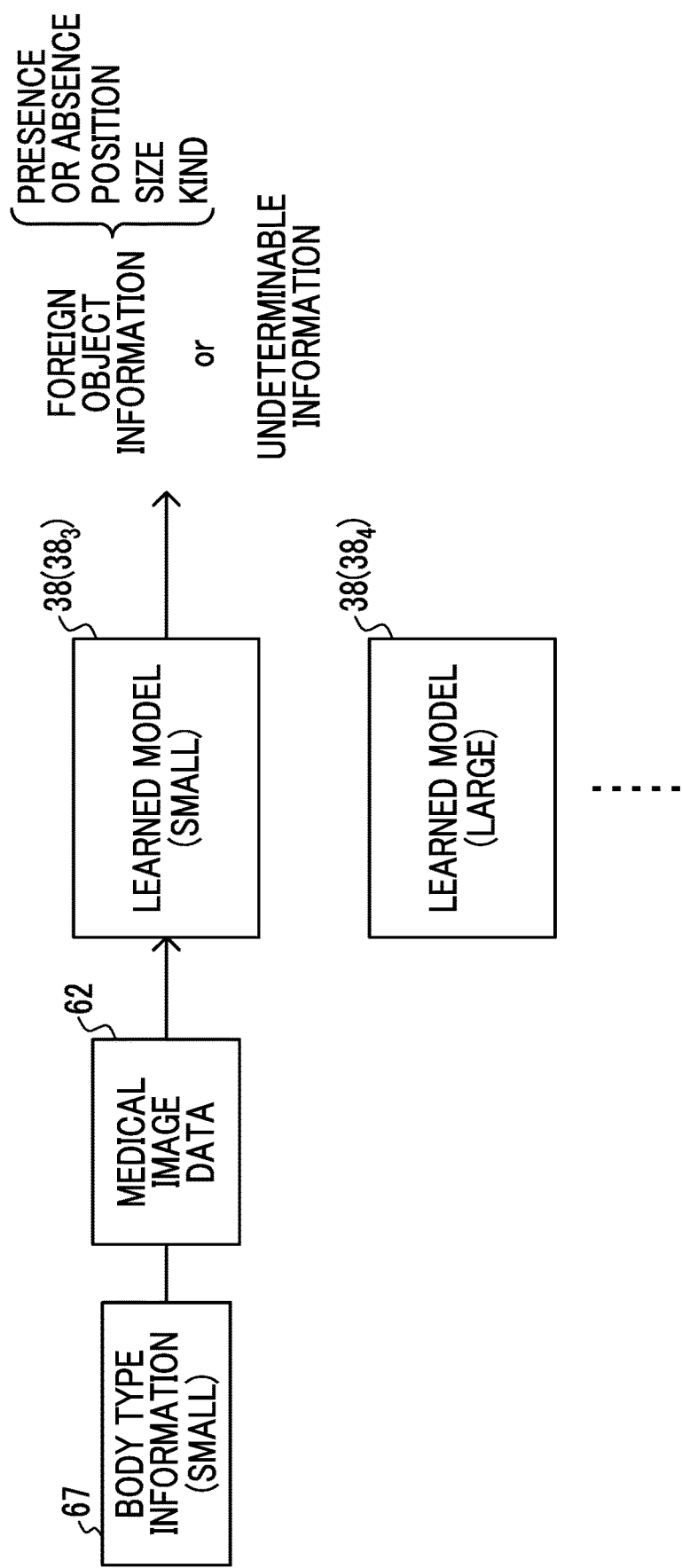
FIG. 19 is a diagram for describing derivation of foreign object information or undeterminable information using a learned model according to a body type in the medical care support device according to the second embodiment.

For example, as shown in FIG. 19, in a case where the body type represented by the body type information 67 in the medical information is "small", the derivation unit 56 inputs the medical image data 62 to the learned model $38_3$ for which the body type is small. The foreign object information or the undeterminable information is output from the learned model $38_3$.

In next step S204, the derivation unit 56 determines whether or not the foreign object is absent in the digestive tract of the subject as described above. On the other hand, in a case where the learned model 38 outputs the foreign object information including the information representing that the foreign object is absent, the determination in step S204 is affirmative, the output unit 57 outputs the derivation result that the foreign object is absent as described above in next step S206, and then the medical care support processing ends.

On the other hand, in a case where the foreign object information output by the learned model 38 does not include the information representing that the foreign object is absent or in a case where the learned model 38 outputs the undeterminable information, the determination in step S204 is negative and the derivation unit 56 determines whether or not the foreign object is present in the digestive tract of the subject as described above in next step S208. In a case where the learned model 38 outputs the foreign object information including the information representing that the foreign object is present, the determination in step S208 is affirmative. In next step S210, the output unit 57 refers to the removal method information 40 ($40_1$ or $40_2$) according to the body type information 67 as described above to acquire the removal method corresponding to the information representing each of the position, size, and kind of the foreign object input from the derivation unit 56 and to output the removal information. Then, the medical care support processing ends.

On the other hand, in a case where the learned model 38 outputs the undeterminable information, the determination in step S208 is negative and the output unit 57 outputs the examination item acquired from the examination item information 42 as described above in next step S212. Then, the medical care support processing ends.

As described above, with the medical care support device 10 according to the present embodiment, it is derived whether or not the foreign object is present in the digestive tract of the subject based on the medical information including the medical image data 62 and the body type information 67, and the learned model 38. With the medical care support device 10 according to the present embodiment, in a case where the foreign object is present in the digestive tract of the subject, it is possible to present the removal method of the foreign object to the user.

With the medical care support device 10 according to the present embodiment, the removal method of the foreign object can be derived according to the body type of the subject. Therefore, it is possible to effectively support the medical care related to the removal of the foreign object in the digestive tract of the subject.

With the medical care support device 10 according to the present embodiment, even in a case where the subject is a hybrid such as a so-called mixed dog or in a case where the dog breed is unknown, the removal method of the foreign object can be derived according to the body type of the subject in consideration of the body type of the subject. Therefore, it is possible to more effectively support the medical care.

Third Embodiment

Hereinafter, a third embodiment will be described in detail.

In the present embodiment, a form in which the medical care support device 10 further provides a removal method according to the age of the subject will be described.

A configuration of the medical care support system 1 according to the present embodiment is the same as the configuration (refer to FIG. 1) of the medical care support system 1 according to the first embodiment, and thus a description thereof will be omitted.

Figure 20:
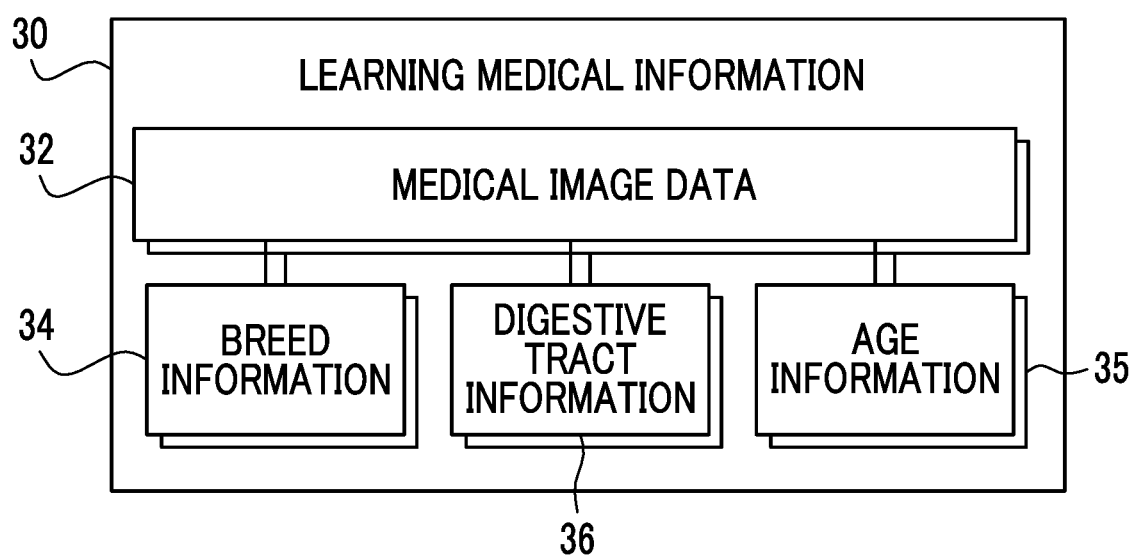
FIG. 20 is a diagram showing an example of learning medical information stored in a storage unit of a medical care support device according to a third embodiment.
Figure 21:
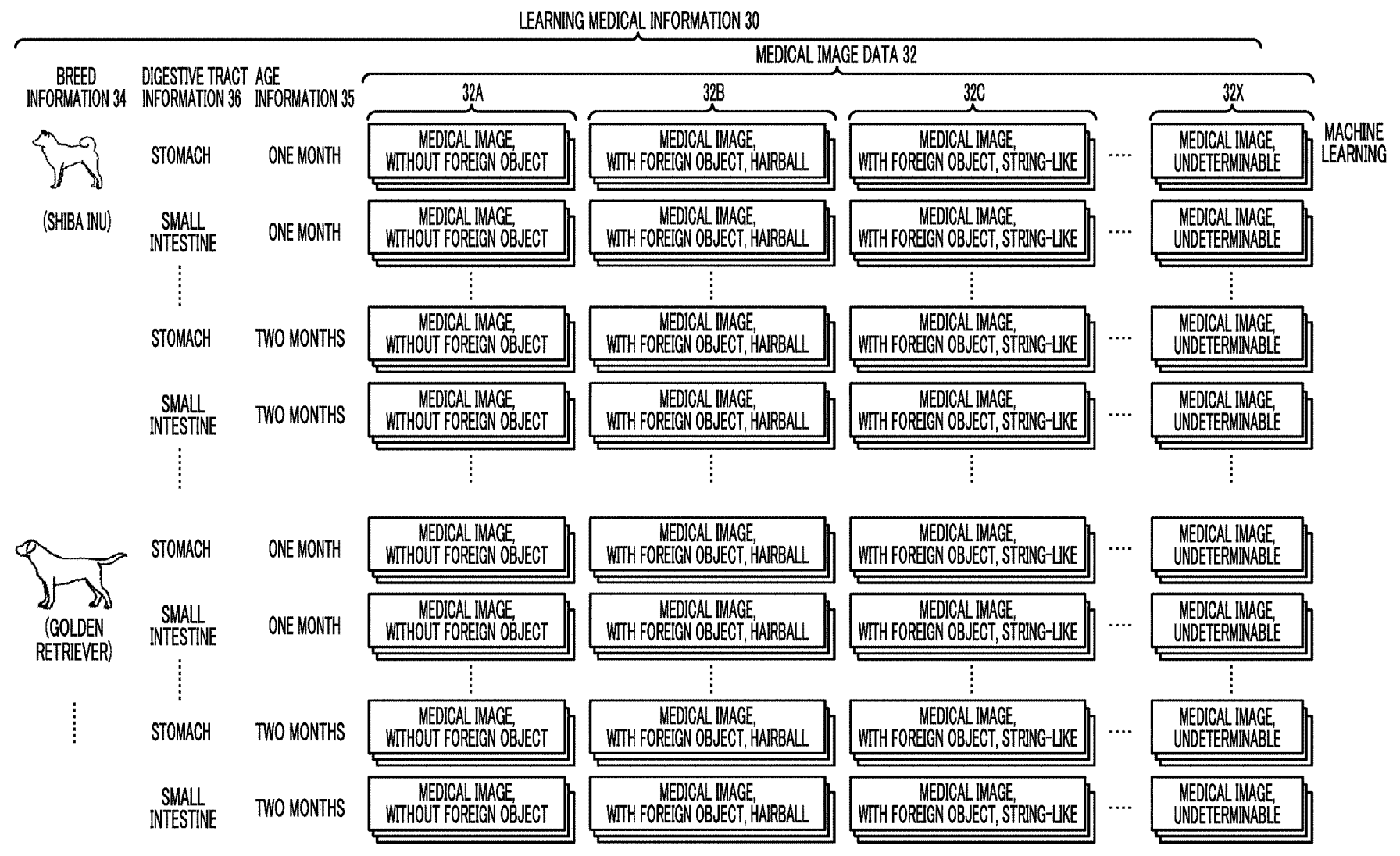

On the other hand, in the medical care support device 10 according to the present embodiment, the contents of the medical information of the subject used for the medical care and the contents of the learning medical information 30 used for learning the learned model 38 are different from those of the first embodiment. Therefore, in the configuration of the medical care support device 10 according to the present embodiment, information included in the learning medical information 30 stored in the storage unit 22 is different from the information (refer to FIGS. 2 and 3) included in the learning medical information 30 stored in the storage unit 22 according to the first embodiment. FIGS. 20 and 21 show an example of the learning medical information 30 according to the present embodiment. As shown in FIGS. 20 and 21, the learning medical information 30 according to the present embodiment includes age information 35 in addition to the breed information 34 and the digestive tract information 36 included in the learning medical information 30 according to the first embodiment.

The age information 35 is age information representing an age of the dog which is the subject and is added to the medical image data 32. The age information 35 is information representing an elapsed time from birth of the subject. In the present embodiment, the age is referred to for convenience, but an elapsed time in month units, that is, a month age is employed instead of an elapsed time in year units from the birth. For example, in a case of the dog or the like, which has a relatively high growth rate, the size of the subject may change significantly with the age in year units. Therefore, in the present embodiment, information representing the month age is employed as the age information 35 as described above. As described above, the elapsed time from the birth of the subject represented by the age information 35 is preferably determined according to the breed or the like of the subject. The time is not limited to the age or the month age and may be, for example, a day age.

Figure 22:
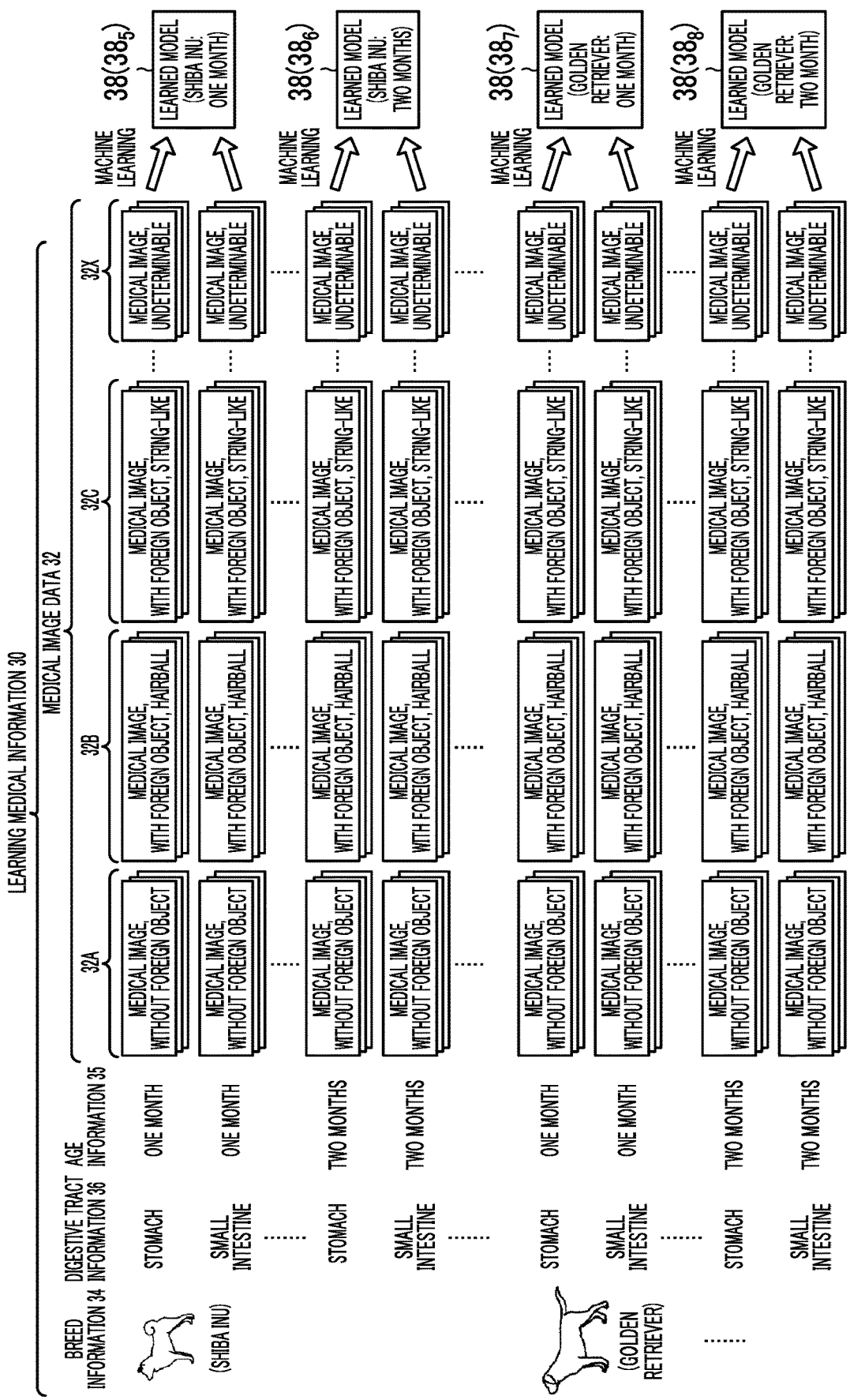
FIG. 22 is a diagram for describing a learned model according to the third embodiment.

As shown in FIG. 22, the learned model 38 according to the present embodiment is generated by machine learning using the learning medical information 30 according to the present embodiment. For example, as shown in FIG. 22, in a case where the dog breed represented by the breed information 34 is "Shiba Inu", a learned model $38_5$ for which the dog breed is Shiba Inu and the age is one month is generated, from the medical image data 32A to 32C and 32X in which the age represented by the age information 35 is "one month" and the digestive tract represented by the digestive tract information 36 is "stomach" and the medical image data 32A to 32C and 32X in which the age represented by the age information 35 is "one month" and the digestive tract represented by the digestive tract information 36 is "small intestine".

For example, as shown in FIG. 22, in a case where the dog breed represented by the breed information 34 is "Shiba Inu", a learned model $38_6$ for which the dog breed is Shiba Inu and the age is two months is generated, from the medical image data 32A to 32C and 32X in which the age represented by the age information 35 is "two months" and the digestive tract represented by the digestive tract information 36 is "stomach" and the medical image data 32A to 32C and 32X in which the age represented by the age information 35 is "two months" and the digestive tract represented by the digestive tract information 36 is "small intestine".

For example, as shown in FIG. 22, in a case where the dog breed represented by the breed information 34 is "Golden Retriever", a learned model $38_7$ for which the dog breed is Golden Retriever and the age is one month is generated, from the medical image data 32A to 32C and 32X in which the age represented by the age information 35 is "one month" and the digestive tract represented by the digestive tract information 36 is "stomach" and the medical image data 32A to 32C and 32X in which the age represented by the age information 35 is "one month" and the digestive tract represented by the digestive tract information 36 is "small intestine". As described above, an example of the learned model 38 includes a neural network model.

FIG. 22 shows the four learned models $38_5$ to $38_8$, the number of learned models 38 to be generated is not limited to four. In a case where the learned models $38_5$ to $38_8$ are collectively referred to without distinction, the symbols "5" to "8" for distinguishing the individual models are omitted and the models are referred to as "learned model 38".

A form may be employed in which one kind of removal method information 40 (refer to FIG. 6) is stored in the storage unit 22 according to the present embodiment as in the first embodiment. However, it is preferable to employ a form in which a plurality of pieces of removal method information 40 are stored for each combination of the dog breed and the age of the subject. As described above, there is a case where the removal method of the foreign object may differ depending on the size (body type) of the body of the subject. The size of the subject differs depending on the breed and the age of the subject, and thus it is preferable to use the plurality of pieces of removal method information 40 for each combination of the dog breed and the age of the subject.

Next, a functional configuration of the medical care support device 10 according to the present embodiment in the learning phase will be described. The overall configuration of the medical care support device 10 according to the present embodiment in the learning phase is the same as that of the medical care support device 10 according to the first embodiment (refer to FIG. 7). On the other hand, there is a difference in a specific operation of the learning unit 52 in the medical care support device 10 according to the present embodiment for generating the learned model 38 based on the learning medical information 30. Therefore, the specific operation of the learning unit 52 will be described.

The learning unit 52 according to the present embodiment generates, by machine learning, a plurality of learned models 38 according to the dog breed and the age that receive the medical image data 32 and output the foreign object information or the undeterminable information in the medical image 33 represented by the medical image data 32, for each of the dog breed of the subject represented by the breed information 34 and the age of the subject represented by the age information 35.

More specifically, in a case where the medical image data 32 to which "Shiba Inu" is added as the dog breed of the subject represented by the breed information 34 and "one month" is added as the age represented by the age information 35 is input, the learning unit 52 causes the model to learn such that the foreign object information or the undeterminable information is output. With the learning, the learned model $38_5$ for which the dog breed is Shiba Inu and the age is one month is generated.

Similarly, in a case where the medical image data 32 to which "Shiba Inu" is added as the dog breed of the subject represented by the breed information 34 and "two months" is added as the age represented by the age information 35 is input, the learning unit 52 causes the model to learn such that the foreign object information or the undeterminable information is output. With the learning, the learned model $38_6$ for which the dog breed is Shiba Inu and the age is two months is generated.

Similarly, in a case where the medical image data 32 to which "Golden Retriever" is added as the dog breed of the subject represented by the breed information 34 and "one month" is added as the age represented by the age information 35 is input, the learning unit 52 causes the model to learn such that the foreign object information or the undeterminable information is output. With the learning, the learned model $38_7$ for which the dog breed is Golden Retriever and the age is one month is generated.

Figure 23:
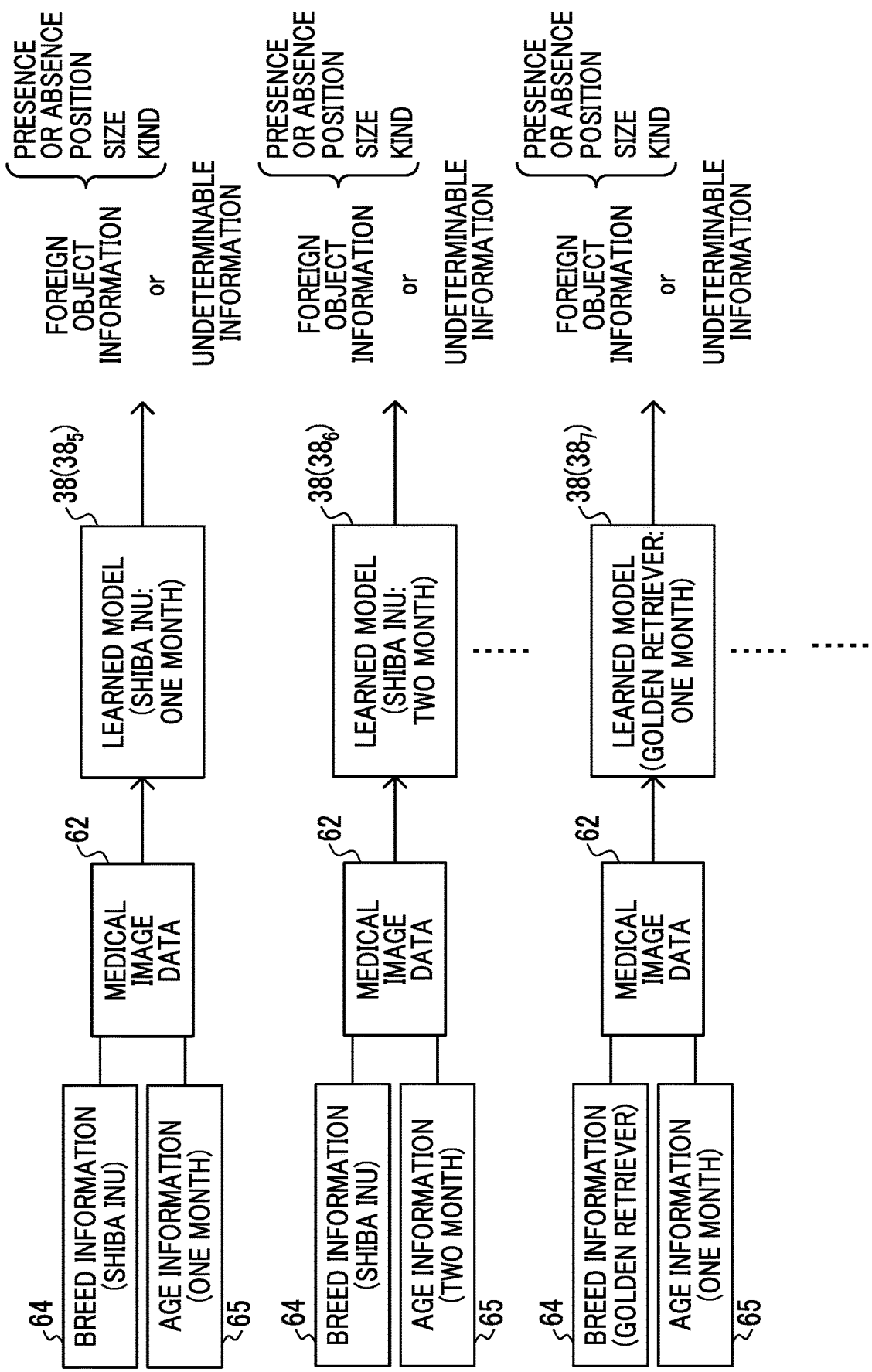
FIG. 23 is a diagram for describing an input and an output of the learned model according to the third embodiment.

For example, as described above, the error back propagation method may be employed as an algorithm of the learning by the learning unit 52 described above. As shown in FIG. 23 as an example, the learned model 38 is generated by the learning by the learning unit 52 described above, which receives the medical image data 62, the breed information 64, and the age information 65 and outputs the foreign object information or the undeterminable information for the foreign object in the medical image represented by the input medical image data 62, for each of the dog breed and the age. The learning unit 52 stores the generated learned model 38 in the storage unit 22.

An action of the medical care support device 10 according to the present embodiment in the learning phase, that is, the learning processing executed by the medical care support device 10 is the same as the learning processing (refer to FIG. 9) executed by the medical care support device 10 according to the first embodiment, and thus the description thereof is omitted.

Figure 24:
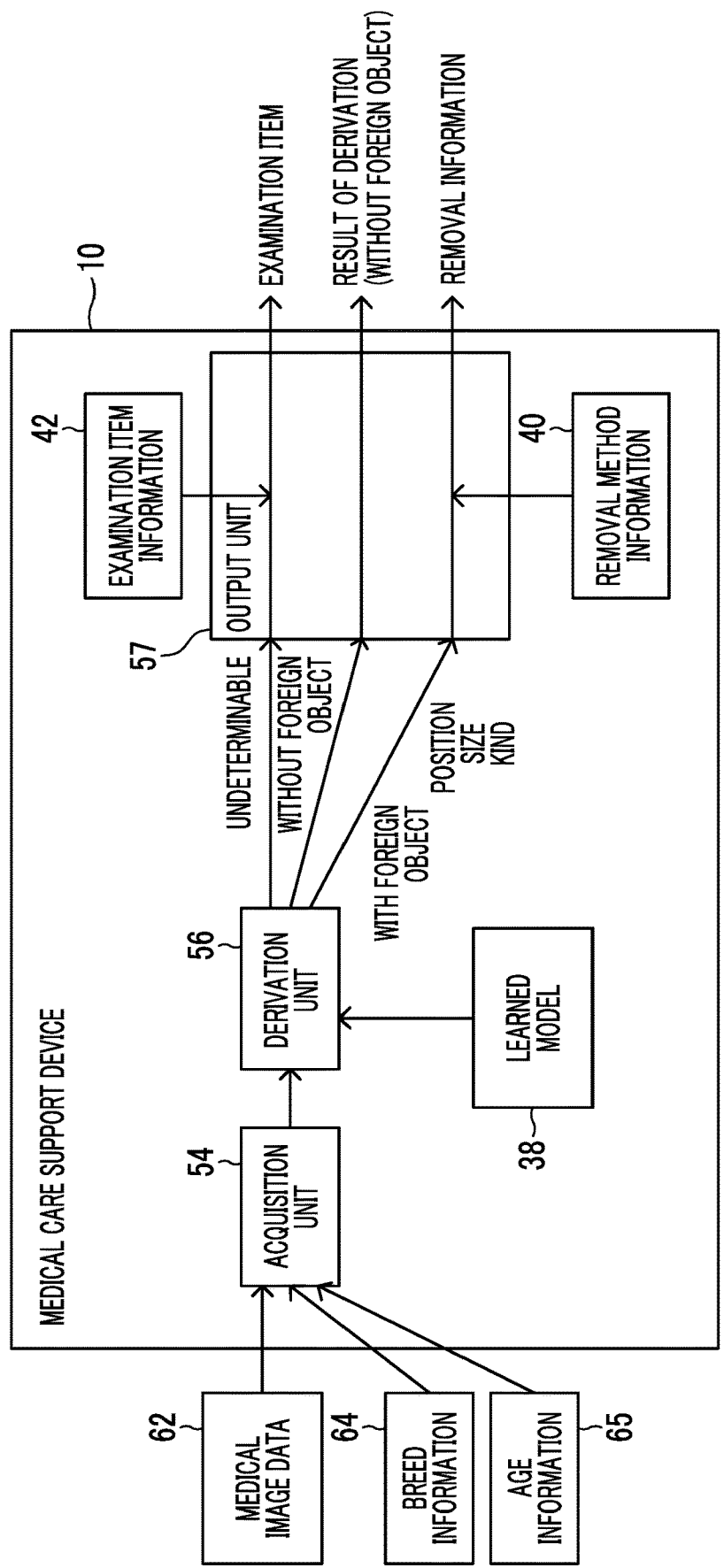
FIG. 24 is a block diagram showing an example of a functional configuration of the medical care support device according to the third embodiment in an operation phase.

Next, a functional configuration of the medical care support device 10 according to the present embodiment in the operation phase will be described with reference to FIG. 24. The medical care support device 10 according to the present embodiment differs from the medical care support device 10 (refer to FIG. 10) according to the first embodiment in specific operations of the acquisition unit 54 and the derivation unit 56. Therefore, the specific operations of the acquisition unit 54 and the derivation unit 56 will be described.

The acquisition unit 54 acquires the medical information including the medical image data 62 representing the medical image in which the subject is captured, the breed information 64 representing the breed of the subject, and the age information 65 representing the age of the subject. The breed information 64 and the age information 65 may be added to the medical image data 62 or may be input by the user through an operation unit (not shown) of the terminal device 12.

The derivation unit 56 derives the information on the foreign object in the digestive tract of the subject based on the medical information (medical image data 62, breed information 64, and age information 65) acquired by the acquisition unit 54 and the learned model 38 learned in advance by the learning medical information 30. Specifically, the derivation unit 56 inputs the medical image data 62 acquired by the acquisition unit 54 to the learned model 38 according to the combination of the dog breed represented by the breed information 64 and the age represented by the age information 65 which are acquired by the acquisition unit 54. The learned model 38 outputs the foreign object information or the undeterminable information according to the input medical information.

As described above, in a case where the plurality of pieces of removal method information 40 are stored in the storage unit 22 of the medical care support device 10 for each combination of the dog breed and the age, the output unit 57 refers to the removal method information 40 according to the combination of the dog breed represented by the breed information 64 and the age represented by the age information 65, which are acquired by the acquisition unit 54, to acquire and output the removal method corresponding to the input information representing each of the position, size, and kind of the foreign object.

Next, an action of the medical care support device 10 according to the present embodiment in the operation phase will be described. The overall flow of the medical care support processing is the same as the medical care support processing shown in FIG. 11 according to the first embodiment and thus will be described with reference to FIG. 11.

In step S200, the acquisition unit 54 acquires the medical information of the dog which is the subject and outputs the medical information to the derivation unit 56. Specifically, the acquisition unit 54 acquires the medical image data 62 representing the medical image obtained by capturing the dog of the subject which is the medical care target by the user using the medical image capturing device, the breed information 64 representing the dog breed of the subject, and the age information 65 representing an age of the subject.

In next step S202, the derivation unit 56 derives the foreign object information based on the medical information input from the acquisition unit 54 and the learned model 38, as described above. Specifically, the derivation unit 56 inputs the medical image data 62 to the learned model 38 selected according to the combination of the dog breed represented by the breed information 64 and the age represented by the age information 65 in the input medical information to acquire the foreign object information or the undeterminable information output from the learned model 38.

For example, as shown in FIG. 25, in a case where the dog breed represented by the breed information 64 in the medical information is "Shiba Inu" and the age represented by the age information 65 is "two months", the derivation unit 56 inputs the medical image data 62 to the learned model $38_6$ for which the dog breed is Shiba Inu and the age is one month. The foreign object information or the undeterminable information is output from the learned model $38_6$.

In next step S204, the derivation unit 56 determines whether or not the foreign object is absent in the digestive tract of the subject as described above. On the other hand, in a case where the learned model 38 outputs the foreign object information including the information representing that the foreign object is absent, the determination in step S204 is affirmative, the output unit 57 outputs the derivation result that the foreign object is absent as described above in next step S206, and then the medical care support processing ends.

On the other hand, in a case where the foreign object information output by the learned model 38 does not include the information representing that the foreign object is absent or in a case where the learned model 38 outputs the undeterminable information, the determination in step S204 is negative and the derivation unit 56 determines whether or not the foreign object is present in the digestive tract of the subject as described above in next step S208. In a case where the learned model 38 outputs the foreign object information including the information representing that the foreign object is present, the determination in step S208 is affirmative. In next step S210, the output unit 57 refers to the removal method information 40 as described above to acquire the removal method corresponding to the information representing each of the position, size, and kind of the foreign object input from the derivation unit 56 and to output the removal information. Then, the medical care support processing ends.

On the other hand, in a case where the learned model 38 outputs the undeterminable information, the determination in step S208 is negative and the output unit 57 outputs the examination item acquired from the examination item information 42 as described above in next step S212. Then, the medical care support processing ends.

As described above, with the medical care support device 10 according to the present embodiment, it is derived whether or not the foreign object is present in the digestive tract of the subject based on the medical information including the medical image data 62, the breed information 64, and the age information 65, and the learned model 38. With the medical care support device 10 according to the present embodiment, in a case where the foreign object is present in the digestive tract of the subject, it is possible to present the removal method of the foreign object to the user.

With the medical care support device 10 according to the present embodiment, it is possible to derive the removal method of the foreign object according to the dog breed and the age of the subject and thus to provide the removal method of the foreign object according to the size or the like of the subject. Therefore, it is possible to more effectively support the medical care related to the removal of the foreign object in the digestive tract of the subject.

As described above, the medical care support device 10 according to the above embodiments comprises the acquisition unit 54, the derivation unit 56, and the output unit 57. The acquisition unit 54 acquires the medical information including the medical image data 62 representing the medical image obtained by capturing the digestive tract of the subject. The derivation unit 56 derives the presence or absence of the foreign object in the digestive tract of the subject, based on the medical information acquired by the acquisition unit 54 and the learned model 38 learned in advance using the plurality of pieces of learning medical information 30 including the medical image data 32 in which the foreign object label 70 according to the kind of the foreign object is assigned to the foreign object in the digestive tract according to each organ of the digestive tract. The derivation unit 56 derives at least one of the position, size, or kind of the foreign object in a case where the foreign object is present. The output unit 57 outputs the removal information representing a predetermined removal method of the foreign object according to at least one of the position, size, or kind of the foreign object in a case where the foreign object is present, based on the derivation result of the derivation unit 56.

There are various kinds and sizes of objects that are accidentally ingested by the subject and become foreign objects. In particular, in a case where the subject is an animal or an infant, an unexpected object may be accidentally ingested. On the other hand, with the medical care support device 10 according to each of the above embodiments, in a case where the foreign object is present in the digestive tract of the subject, the removal method of the foreign object is output based on the medical information including the medical image data 62 and the breed information 64 and the learned model 38. Therefore, with the medical care support device 10 according to each of the above embodiments, it is possible to effectively support the medical care related to the removal of the foreign object in the digestive tract of the subject.

In a case where it is specifically known what the foreign object in the digestive tract of the subject is and in the case of urgency, the removal method is not limited to the removal method output by the medical care support device 10 according to the present embodiment and it is preferable to perform prompt removal by the laparotomy or the like.

The learned model 38 is not limited to the model shown in each of the above embodiments. For example, a form may be employed in which the medical care support device 10 comprises the plurality of learned models 38 for each digestive tract represented by the digestive tract information 36. As an example of this case, in FIG. 26, a form is shown in which the learned model 38 is generated by machine learning using the learning medical information 30 including the medical image data 32, the breed information 34, and the digestive tract information 36, for each combination of the dog breed represented by the breed information 34 and the digestive tract represented by the digestive tract information 36. For example, as shown in FIG. 26, in a case where the dog breed represented by the breed information 34 is "Shiba Inu", a learned model $38_9$ for which the dog breed is Shiba Inu and the digestive tract is stomach is generated from the medical image data 32A to 32C and 32X in which the digestive tract represented by the digestive tract information 36 is "stomach". A learned model $38_{10}$ for which the dog breed is Shiba Inu and the digestive tract is small intestine is generated from the medical image data 32A to 32C and 32X in which the digestive tract represented by the digestive tract information 36 is "small intestine". Similarly, in a case where the dog breed represented by the breed information 34 is "Golden Retriever", a learned model $38_{11}$ for which the dog breed is Golden Retriever and the digestive tract is stomach is generated, from the medical image data 32A to 32C and 32X in which the digestive tract represented by the digestive tract information 36 is "stomach". A learned model $38_{12}$ for which the dog breed is Golden Retriever and the digestive tract is small intestine is generated from the medical image data 32A to 32C and 32X in which the digestive tract represented by the digestive tract information 36 is "small intestine". In the case of the form shown in FIG. 26, the acquisition unit 54 acquires the medical information including the medical image data 62, breed information 64, and the age information 65. The derivation unit 56 inputs the medical image data 62 to the learned model 38 selected according to the combination of the dog breed represented by the breed information 64 and the age represented by the age information 65 to acquire the foreign object information or the undeterminable information output from the learned model 38.

Various types of information included in the learning medical information 30 used for generating the learned model 38 are not limited to the above embodiments. For example, the learning medical information 30 in the above embodiments may be combined.

In the above embodiments, a form in which the dog is employed as the subject is described, but the subject is not limited thereto. For example, a human may be employed as the subject, or an animal other than the dog such as a cat may be employed.

The following various processors may be used as a hardware structure of a processing unit that executes various types of processing such as each functional unit of the medical care support device 10 in the above embodiments. The various processors include a programmable logic device (PLD) which is a processor whose circuit configuration is changeable after manufacturing such as a field-programmable gate array (FPGA), a dedicated electric circuit which is a processor having a circuit configuration exclusively designed to execute specific processing such as an application specific integrated circuit (ASIC), and the like, in addition to the CPU which is a general-purpose processor that executes software (program) to function as various processing units as described above.

One processing unit may be configured by one of the various processors or a combination of two or more processors of the same type or different types (for example, a combination of a plurality of FPGAs or a combination of a CPU and an FPGA). A plurality of processing units may be configured by one processor.

As an example of configuring the plurality of processing units with one processor, first, there is a form in which one processor is configured by a combination of one or more CPUs and software and the processor functions as the plurality of processing units, as represented by computers such as a client and a server. Second, there is a form in which a processor that realizes the functions of the entire system including the plurality of processing units with one integrated circuit (IC) chip is used, as represented by a system-on-chip (SoC) or the like. As described above, the various processing units are configured using one or more of the various processors as the hardware structure.

Further, more specifically, a circuitry combining circuit elements such as semiconductor elements can be used as the hardware structure of the various processors.

Further, in the above embodiment, the learning program 23A and the medical care support program 23B are stored (installed) in the storage unit 22 in advance, but the present disclosure is not limited thereto. Each of the learning program 23A and the medical care support program 23B may be provided in a form of being recorded on a recording medium such as a compact disc read only memory (CD-ROM), a digital versatile disc read only memory (DVD-ROM), and a Universal Serial Bus (USB) memory. Each of the learning program 23A and the medical care support program 23B may be configured to be downloaded from an external device through a network.

The following appendix is disclosed with regard to the above embodiments.

Appendix 1

A medical care support device comprising:
    an acquisition unit that acquires a plurality of pieces of learning medical information including medical image data in which a label according to a kind of a foreign object is assigned to the foreign object in a digestive tract according to each organ of the digestive tract; and
    a learning unit that generates a learned model that outputs foreign object information including presence or absence of the foreign object in the digestive tract of a subject and information representing at least one of position, size, or kind of the foreign object with learning using the plurality of pieces of learning medical information.

What is claimed is:

1. A medical care support device comprising:
    an acquisition unit that acquires medical information including medical image data representing a medical image obtained by capturing a digestive tract of a subject;
    a derivation unit that derives presence or absence of a foreign object in the digestive tract of the subject, based on the medical information acquired by the acquisition unit and an automated learned model generated in advance using a plurality of pieces of learning medical information including the medical image data in which a label according to a kind of the foreign object is assigned to the foreign object in the digestive tract according to each organ of the digestive tract, and derives at least one of position, size, or kind of the foreign object in a case where the foreign object is present; and an output unit that outputs removal information representing a predetermined removal method of the foreign object from the digestive tract of the subject according to the at least one of position, size, or kind of the foreign object in a case where the foreign object is present, based on a result of the derivation of the derivation unit.

2. The medical care support device according to claim 1, wherein the medical information further includes breed information representing a breed of the subject, and
wherein the learning medical information further includes the breed information.

3. The medical care support device according to claim 1, wherein the medical information further includes body type information representing a kind relating to a body type of the subject, and
wherein the learning medical information further includes the body type information.

4. The medical care support device according to claim 1, wherein the medical information further includes age information representing an age of the subject, and
wherein the learning medical information further includes the age information.

5. The medical care support device according to claim 1, wherein a plurality of pieces of the learning medical information used for learning of the learned model further include learning medical information including medical image data to which a label representing that determination related to the foreign object is impossible is assigned, and
wherein the derivation unit further derives that determination related to the foreign object in the digestive tract of the subject is impossible based on the medical information acquired by the acquisition unit and the learned model.

6. The medical care support device according to claim 5, wherein the output unit outputs examination item information representing a predetermined examination item in a case where the derivation unit derives that the determination is impossible.

7. The medical care support device according to claim 1, wherein the foreign object is a non-lesion.

8. A medical care support method executed by a computer, comprising:
acquiring medical information including medical image data representing a medical image obtained by capturing a digestive tract of a subject;
deriving presence or absence of a foreign object in the digestive tract of the subject based on the medical information acquired by the acquisition unit and an automated learned model generated in advance using a plurality of pieces of learning medical information including the medical image data in which a label according to a kind of the foreign object is assigned to the foreign object in the digestive tract according to each organ of the digestive tract;
deriving at least one of position, size, or kind of the foreign object in a case where the foreign object is present; and
outputting removal information representing a predetermined removal method of the foreign object from the digestive tract of the subject according to the at least one of position, size, or kind of the foreign object in a case where the foreign object is present, based on a result of the derivation.

9. A non-transitory storage medium storing a program that causes a computer to execute medical care support processing, the processing comprising:
acquiring medical information including medical image data representing a medical image obtained by capturing a digestive tract of a subject;
deriving presence or absence of a foreign object in the digestive tract of the subject based on the medical information acquired by the acquisition unit and an automated learned model generated in advance using a plurality of pieces of learning medical information including the medical image data in which a label according to a kind of the foreign object is assigned to the foreign object in the digestive tract according to each organ of the digestive tract;
deriving at least one of position, size, or kind of the foreign object in a case where the foreign object is present; and
outputting removal information representing a predetermined removal method of the foreign object from the digestive tract of the subject according to the at least one of position, size, or kind of the foreign object in a case where the foreign object is present, based on a result of the derivation.

* * * * *